(12) United States Patent
Leonard et al.

(10) Patent No.: US 10,456,183 B2
(45) Date of Patent: Oct. 29, 2019

(54) DEVICE IN THE FORM OF A KIT FOR MIXING AND INJECTING A BONE CEMENT

(71) Applicant: TEKNIMED, Vic en Bigorre (FR)

(72) Inventors: Alain Leonard, Nosy Be (MG); Carole Leonard, Paulhac (FR); Gautier Halbin, Toulouse (FR); Cyril Sender, Toulouse (FR)

(73) Assignee: TEKNIMED, Vic en Bigorre (FR)

( * ) Notice: Subject to any disclaimer, the term of this patent is extended or adjusted under 35 U.S.C. 154(b) by 340 days.

(21) Appl. No.: 15/537,093

(22) PCT Filed: Dec. 21, 2015

(86) PCT No.: PCT/FR2015/053697
§ 371 (c)(1),
(2) Date: Jun. 16, 2017

(87) PCT Pub. No.: WO2016/097665
PCT Pub. Date: Jun. 23, 2016

(65) Prior Publication Data
US 2017/0340372 A1     Nov. 30, 2017

(30) Foreign Application Priority Data
Dec. 19, 2014   (FR) ...................................... 14 62974

(51) Int. Cl.
| *A61B 17/58* | (2006.01) |
| *A61B 17/60* | (2006.01) |
| *A61F 2/00* | (2006.01) |
| *A61B 17/88* | (2006.01) |
| *A61L 24/00* | (2006.01) |
| *A61M 5/20* | (2006.01) |

(52) U.S. Cl.
CPC ...... *A61B 17/8805* (2013.01); *A61B 17/8802* (2013.01); *A61B 17/8822* (2013.01); *A61L 24/001* (2013.01); *A61M 5/2066* (2013.01); *A61L 2400/06* (2013.01); *A61L 2430/02* (2013.01)

(58) Field of Classification Search
None
See application file for complete search history.

(56) References Cited

U.S. PATENT DOCUMENTS

| 2005/0105385 A1* | 5/2005 | McGill | .............. A61B 17/8805 366/139 |
| 2011/0114212 A1 | 5/2011 | Greter et al. | |
| 2013/0079786 A1 | 3/2013 | Bonnin et al. | |

FOREIGN PATENT DOCUMENTS

| EP | 1 614 403 A1 | 1/2006 |
| FR | 2 967 344 A1 | 5/2012 |
| WO | WO 2005/048886 A2 | 6/2005 |

* cited by examiner

*Primary Examiner* — Sameh R Boles
(74) *Attorney, Agent, or Firm* — Birch, Stewart, Kolasch & Birch, LLP

(57) ABSTRACT

A device in the form of a kit for mixing and injecting a bone cement is described, in which a mixing unit and a transfer unit are two units distinct from and independent of each other, with no element in common, and are designed to be connected alternately, that is to say successively, to the same end of a hollow cylindrical body or mixing body of a main module, before this main module is connected to an injection unit via its other end.

11 Claims, 22 Drawing Sheets

DEVICE IN THE FORM OF A KIT FOR MIXING AND INJECTING A BONE CEMENT

FIELD OF THE INVENTION

The present invention relates generally to devices used in bone surgery, and more particularly to a kit-type device for mixing and injecting a bone cement.

TECHNOLOGICAL BACKGROUND

Bone cement is injected during various surgical procedures, such as vertebroplasty procedures, in order to consolidate the structure of the bone after injury, natural wear or degeneration due to a degenerative disease.

The bone cements currently used have the specificity of being composed of at least two substances, a powder and a liquid, which need to be mixed so as to obtain a homogeneous composition. In order to strengthen and reinforce, for example, a weakened vertebra, the cement formed in this way must subsequently be inserted by injection into the vertebral body of the vertebra to be treated.

PRIOR ART

Devices suitable for both the production of the mixture of the bone cement components and, subsequently, the transcutaneous injection of the bone cement thus obtained at the target site in the patient's body are known.

For example, document WO 2005/048886 discloses various embodiments of an apparatus for mixing and injecting bone cement. The apparatus comprises a first cylindrical body with a mixing chamber, along with a second cylindrical body with a discharge chamber. The cement is produced in the mixed chamber. The discharge chamber can then be placed in fluidic communication with the mixing chamber, in order to receive the bone cement. The bone cement is then injected into the patient's body from the discharge chamber.

However, the proposed apparatuses have a complex design. The use thereof can for this reason prove to be risky, whereas a surgical procedure cannot suffer from any kind of hazards regarding the surgical equipment used and the availability of the bone cement at the specific time when the practitioner needs it in order to carry out the injection.

SUMMARY OF THE INVENTION

The aim of the invention is that of eliminating, or at least reducing, all or some of the drawbacks of the prior art cited above, by proposing a device for mixing and injecting a bone cement which is simpler to use.

For this purpose, a first aspect of the invention relates to a kit-type device for mixing and injecting a bone cement, comprising a main module, on the one hand, and accessories comprising a removable closing cap and a plurality of functional modules, on the other hand, each of said accessories being adapted to be connected or not to the main module according to respective phases of use of the device, wherein:

the main module is a hollow cylindrical body having a proximal end and a distal end that are open, each adapted to be connected to one or a plurality of the accessories of the device, according to the phases of use;

one of the functional modules is a mixing unit, adapted to be connected, in a mixing phase, to the proximal end of the main module while the distal end of said main module is closed by the closing cap, and to enable a user to mix at least two compounds of the bone cement in the body of the main module;

a further functional module is an injection unit, adapted to be connected, in a transfer phase following the mixing phase as well as in an injection phase following said transfer phase, to the distal end of the main module instead of the closing cap, and to enable the user to inject the bone cement;

a further functional module, distinct from the mixing unit and with no common element with the mixing unit, is a transfer unit, adapted to be connected, in the transfer phase, to the proximal end of the main module instead of the mixing unit and to enable the user to transfer bone cement from the body of the main module to the injection unit.

The simplicity of the proposed device in comparison with the apparatuses according to the prior art lies in that it is a kit-type device of a particularly accomplished type, wherein the mixing unit and the transfer unit are two units distinct from and independent of each other, with no element in common, and adapted to be connected in turn, that is to say successively, to the same end of the cylindrical body of the main module or mixing body. However, the mixing body of the main module ensures the transition, in that the mixture produced therein by the mixing unit is subsequently expelled therefrom by the transfer unit, without requiring any intervention of the user apart from the disconnection of the mixing unit and the connection of the transfer unit instead of said mixing unit.

In a second aspect, the invention also relates to a method for using the kit according to the first aspect, more particularly a method for mixing and injecting a bone cement using a kit-type device comprising a main module in the form of a hollow cylindrical body with a proximal end and a distal end that are open, on the one hand, and accessories comprising a removable closing cap and a plurality of functional modules, on the other hand, the method comprising steps consisting in:

a) in a mixing phase, connecting one of the functional modules or mixing unit to the main module while the distal end of said main module is closed by the closing cap, and mixing at least two compounds of the bone cement in the body of the main module;

b) in a transfer phase following the mixing phase:

b1) connecting another functional module or transfer unit, distinct from the mixing unit and with no common element with the mixing unit, to the proximal end of the main module instead of the mixing unit, and b2) connecting another functional module or injection unit to the distal end of the main module instead of the closing cap, b3) transferring bone cement from the body of the main module to the injection unit; and, c) in an injection phase following the transfer phase, injecting the bone cement.

None of the elements of the mixing unit involved in the mixing function is liable to interfere with any element of the transfer unit. Conversely, none of the elements of the transfer unit involved in the cement transfer function in the injection unit (or syringe) is liable to interfere with any element of the mixing unit. The risk of a malfunction or a handling error that can result in the failure of the operations of mixing and transferring the cement produced in the syringe is thereby reduced.

BRIEF DESCRIPTION OF THE DRAWINGS

Further features and advantages of the invention will become apparent on reading the following description. This description is merely illustrative and should be read with reference to the appended drawings wherein.

DETAILED DESCRIPTION OF EMBODIMENTS

Figure 1:
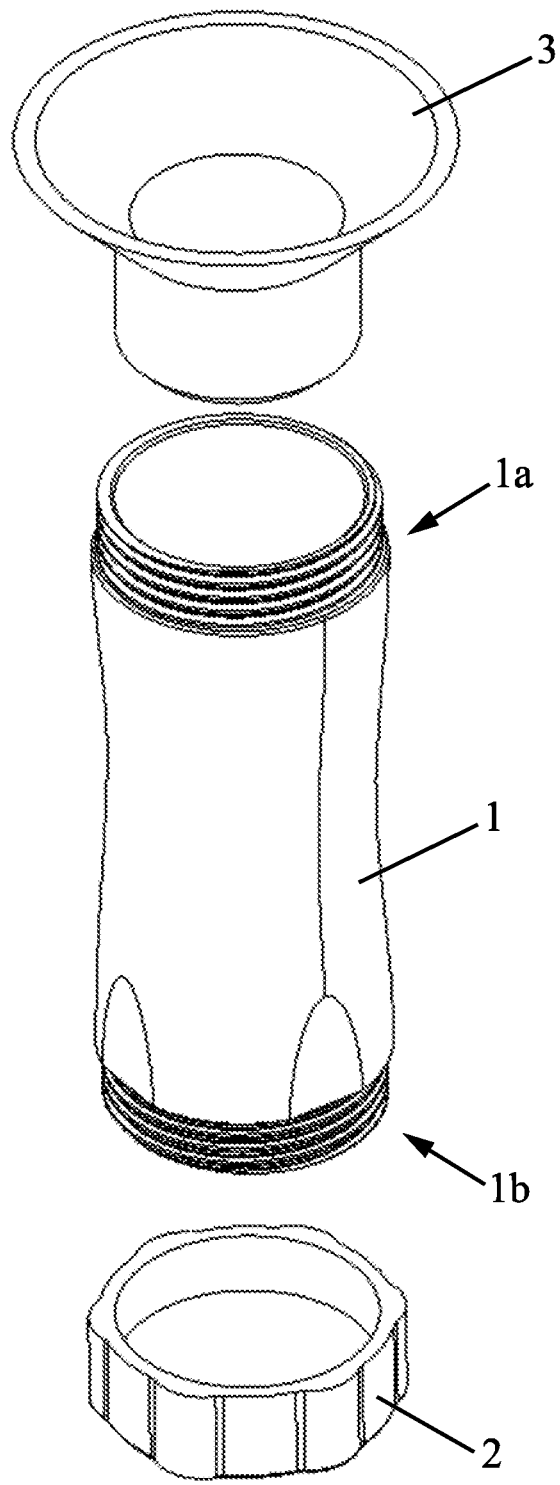
FIG. 1 is a three-dimensional view of an embodiment of the main module of the device with two of the accessories thereof.

In the drawings and in the following description, the same elements are referred to by the same reference signs as in the figures of the drawings.

Embodiments of a kit-type device for mixing and injecting a bone cement, and a method for using said kit will be described.

Such a kit can be used in a surgical environment for repairing bone and joint injuries, for example for filling spongy bone tissue or for helping fix artificial implants to a patient's skeleton.

In such bone surgery applications (cementoplasty), the kit enables both the preparation and the injection, at a target site, of a fluid cement for medical use having suitable mechanical, chemical and biocompatibility properties, for example acrylic cement.

A percutaneous vertebroplasty surgical procedure, for example, consists in injecting under radioscopic or CT scan monitoring, a cement into a vertebra that is weakened, fractured or has any other bone lesion, in order to consolidate it. Further applications of the kit comprise kyphoplasty, which consists in injecting cement into the vertebral body previously treated with inflatable balloons, with the intention of restoring a portion of the volume thereof to the compressed vertebrae.

Such bone cements are organic polymers having variable compositions, for example a methacrylate polymer based composition. The organic polymers can be produced from a binary mixture, for example from a pre-polymer, generally PMMA (polymethyl methacrylate), and a monomer, generally MMA (methyl methacrylate), reacting in the presence of a polymerization activator along with optionally further adjuvants, according to the envisaged applications.

Most of the available cements are presented in the form of two separate components. On the one hand, a powder essentially comprising pre-polymer beads. On the other hand, a liquid essentially containing the monomer. The initiator, for example benzoyl peroxide (BPO), is generally incorporated into the powder, whereas the liquid contains a chemical activator (catalyst) such as di-methyl-para-toluidine (DPMT). The polymerization reaction starts when the two components are mixed.

The kit for mixing and injecting a bone cement comprises a main module, on the one hand, and accessories, on the other hand, each of said accessories being adapted to be connected or not to the main module according to respective phases of use of the device.

The accessories comprise a plurality of functional modules, including a mixing unit (or mixer), an injection unit (or syringe), and a transfer unit, which will be described further hereinafter. They also comprise a removable closing cap for the main module, and preferably also a funnel, which is however not essential.

Figure 2:
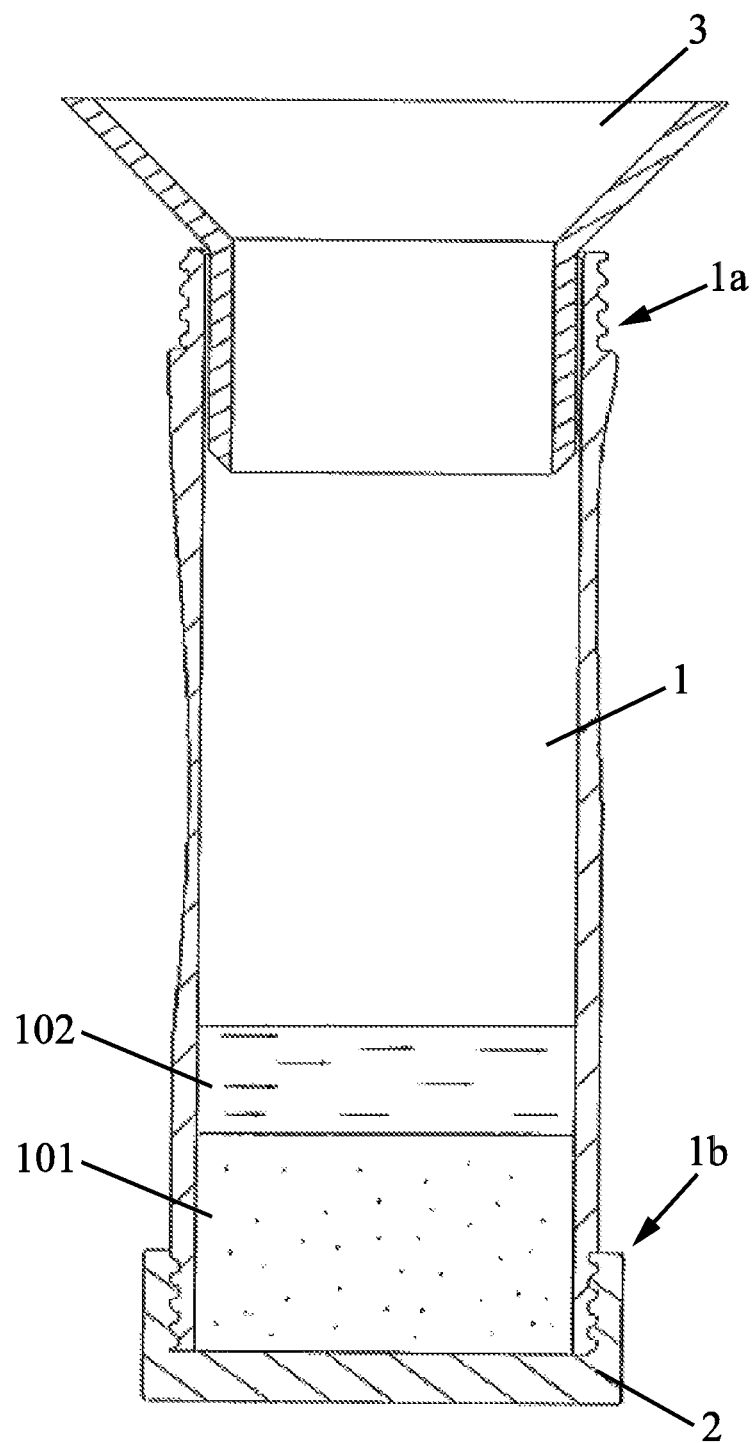
FIG. 2 is a sectional view of the module of FIG. 1 with the two accessories fitted thereon.

With reference to FIGS. 1 and 2, the main module 1 has for example the shape of a hollow cylindrical body, having an internal wall, an open proximal end 1a and an open distal end 1b. In other words, the cylindrical body 1 is open at each of its ends 1a and 1b.

The distal end 1b has an opening with a diameter equal to the diameter of the cylinder formed by the internal wall of the main module 1.

The components of the bone cement are mixed in this cylindrical body 1, which is also referred to hereinafter as the mixing body.

According to one embodiment, the main module 1 can have a continuous or discontinuous internal screw thread on the internal wall or a continuous or discontinuous screw thread on the external wall of the main module at the proximal 1a and distal 1b ends. These screw threads are used for connecting the main module to one of the accessories, such as for example the illustrated closing cap 2. To this end, the cap has respectively a screw thread on the external face thereof or a complementary internal screw thread on the internal face thereof. When connected in this way to the distal end 1b, the cap 2 closes the mixing body 1 at this end 1b, as shown in FIG. 2. The closure produced thereby is water tight. When needed, a seal not shown ensures, or contributes to this water tightness, for example an O-ring arranged in the base part of the cap 2 to press against the periphery of the distal end 1b of the mixing body 1.

According to the phases of use, two of the accessories of the kit can be simultaneously connected to the mixing body 1, one to each of its ends. In addition, and as described hereinafter, more than one of the accessories can be connected to the same end of the mixing body 1, in succession.

In the embodiments described herein, the accessories of the kit are connected to the main module by screw threads, preferably with seals ensuring water tightness. This is however not the only means of obtaining this connection. The connection can also be obtained, for example, by snap-fit means using mutually complementary means provided on the main module and on the accessories.

As shown in FIG. 2, the cylindrical part of the funnel 3 can be simply inserted inside the mixing body 1, at the proximal end 1a, with no connection. To this end, the external diameter of the cylindrical part of the funnel 3 is slightly less than the internal diameter of the mixing body 1, the frustoconical and flared part of the funnel 3 then projecting outside said mixing body 1 and thereby holding the funnel in a stable position under the effect of gravity alone when the main module is positioned or held upright, as shown in FIG. 2. Alternatively, the funnel can be adapted to connect to the proximal end 1a of the mixing body 1. To this end, the cylindrical part of the funnel can, for example, have an internal screw thread which is complementary with the external screw thread of the mixing body 1 provided at the end 1a for connecting other accessories to the main module.

In a loading phase of the components of the bone cement into the mixing body 1, optionally using the funnel 3, the user pours into said body, via the proximal end 1a thereof, the components to be mixed to form the bone cement. They consist essentially, as shown in FIG. 2, of the powder 101 essentially comprising pre-polymer beads and of the liquid 102 essentially containing the monomer.

During this operation, the other end of the mixing body 1, that is to say the distal end 1b thereof, is closed by the cap 2.

The use of the funnel prevents any loss of either of the products to be mixed, which could affect the final composition of the cement once mixed.

After the two substances are poured into the mixing body 1, the funnel 3 is removed to give way to another accessory, that is to say a mixing unit.

Figure 3:
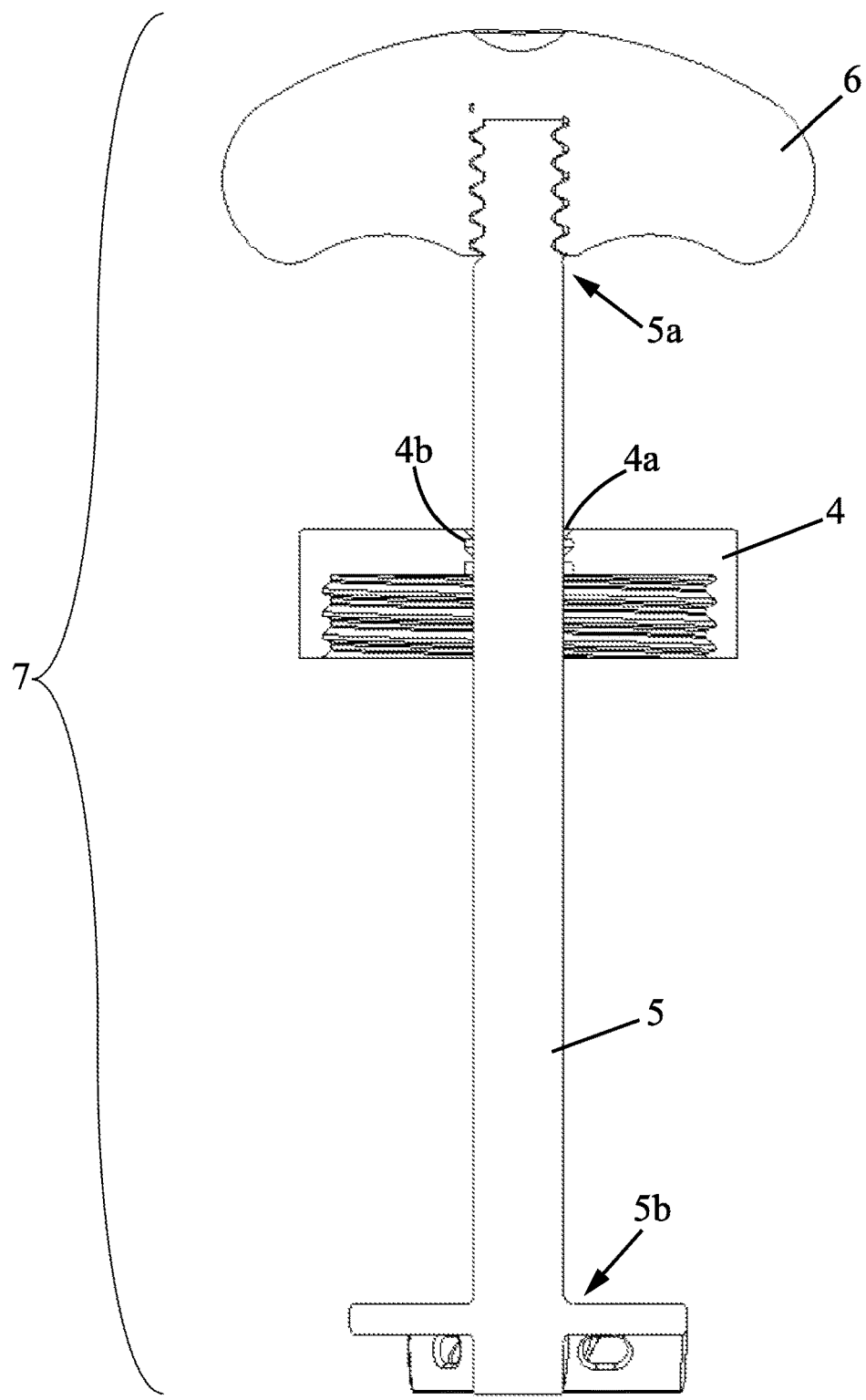
FIG. 3 is a sectional view of the mixing unit of FIG. 4.
Figure 4:
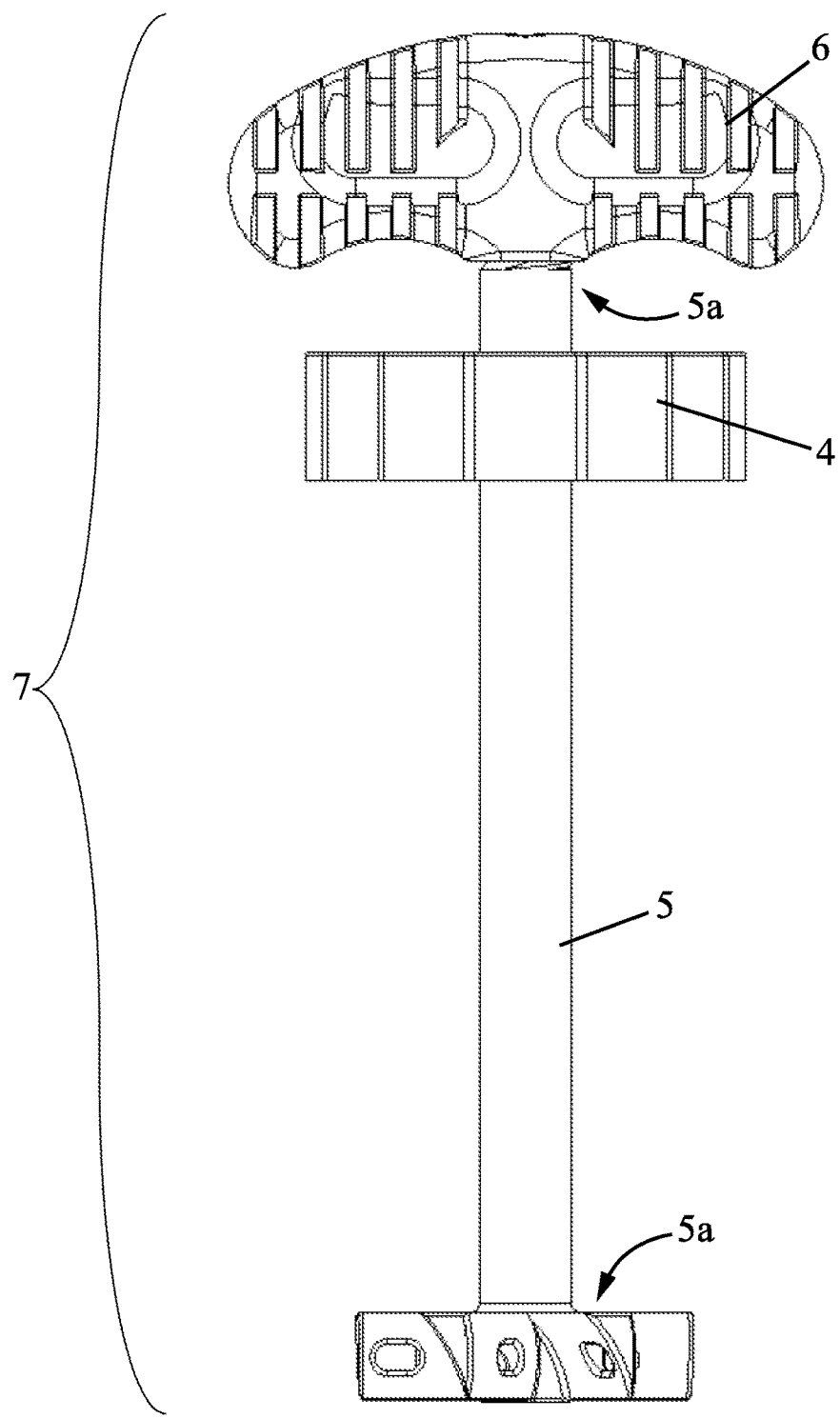
FIG. 4 is a side view of an embodiment of the mixing unit.
Figure 5:
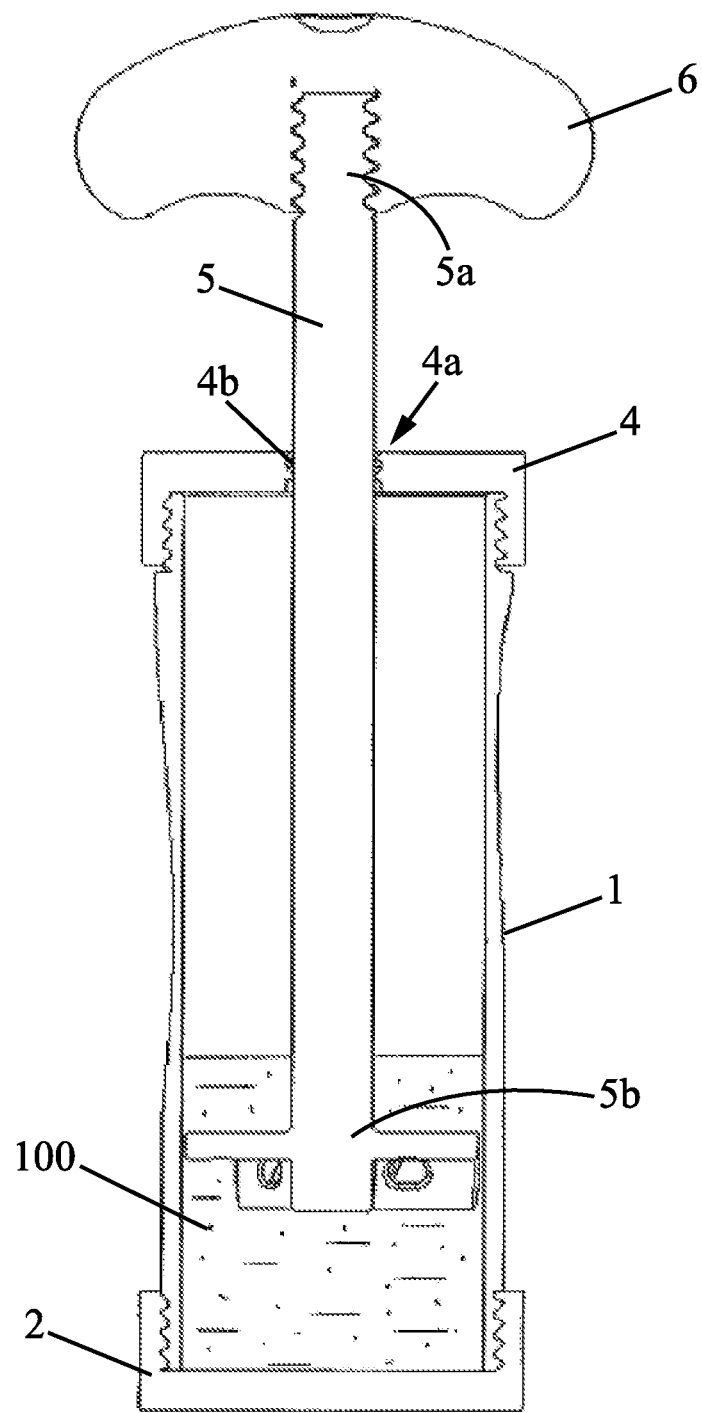
FIG. 5 is a sectional view of the mixing unit of FIG. 4 connected to the main module of FIG. 1.
Figure 6:
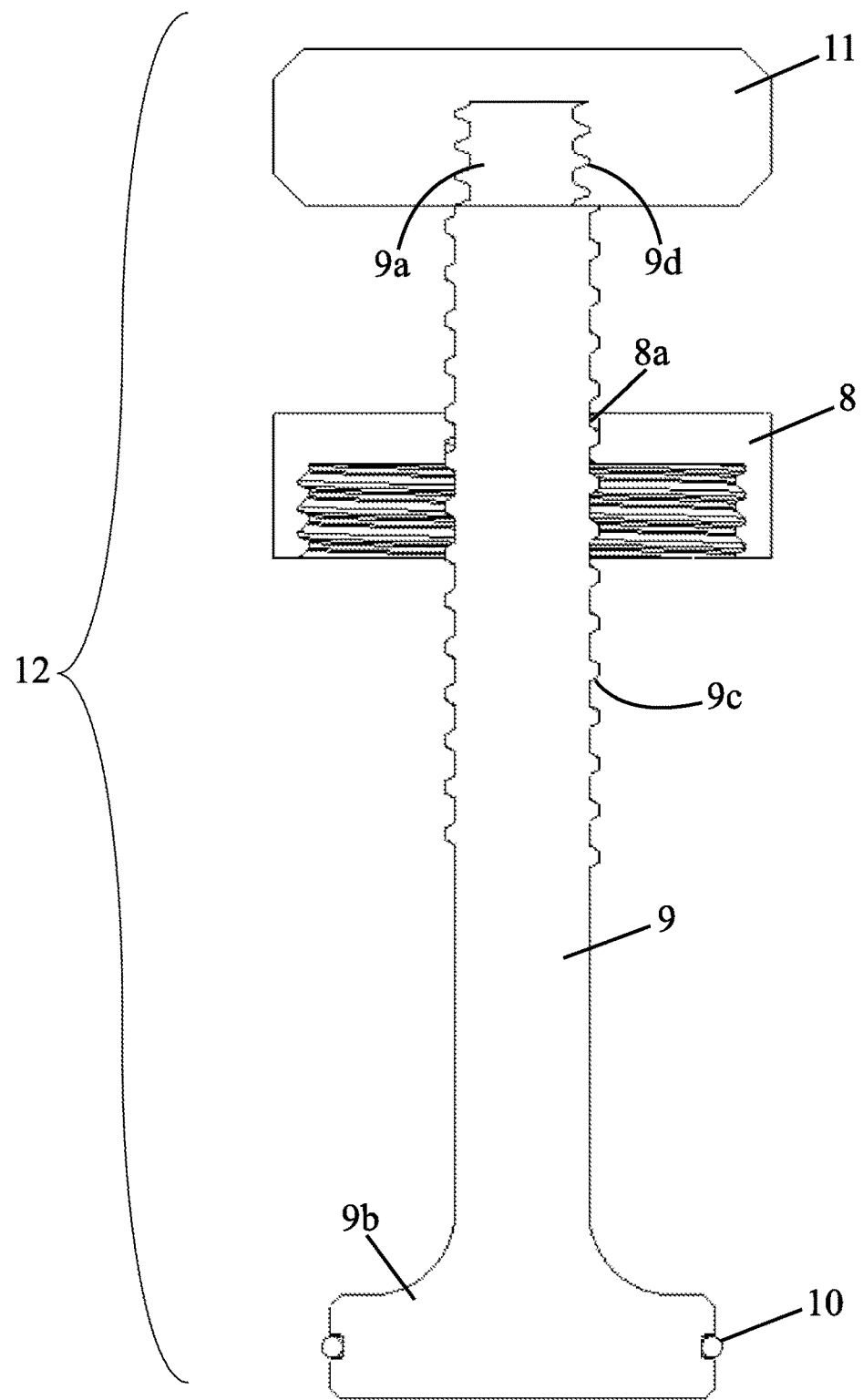
FIG. 6 is a sectional view of the transfer unit of FIG. 7.
Figure 7:
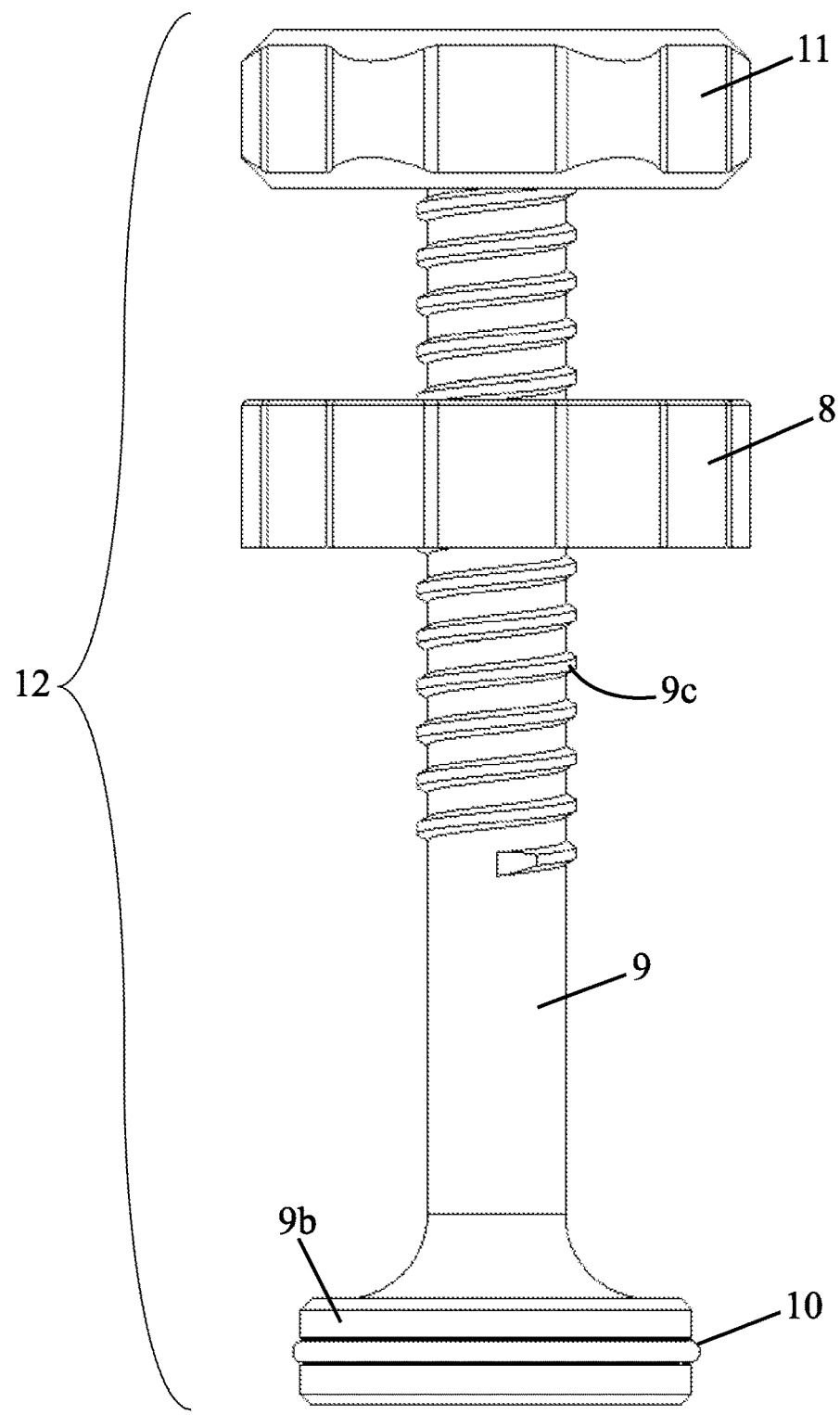
FIG. 7 is a side view of an embodiment of the transfer unit.

With reference to FIGS. 3, 4 and 5, one of the functional modules is indeed a mixing unit, or mixer 7. The function of the mixer 7 is to enable the user to mix the components 101 and 102 of the bone cement in the body of the main module 1. To this end, the mixer 7 is adapted to be connected, in a mixing phase, to the proximal end 1a of the mixing body 1 whereas the distal end 1b of said mixing body is still closed by the closing cap 2.

The mixer 7 comprises a cap 4, and an actuation rod 5 passing through said cap.

The cap 4 is adapted to close the proximal end 1a of the mixing body 1 when the mixing unit 7 is connected to said main module. In order to make this connection, the cap 4 can comprise a internal screw thread complementary with the external screw thread of the proximal end 1a of the mixing body 1.

The actuation rod 5 is in the form of an elongated body, for example made of solid material, having an outwardly smooth appearance, of cylindrical shape, with a diameter substantially less than the internal diameter of the mixing body 1, and a corresponding length approximately equal to or greater than the length of said body along its longitudinal axis.

At one of its ends 5b intended to plunge into the body of the main module when the mixer 7 is connected to the main module 1, the actuation rod 5 comprises mixing blades, for example openwork blades as shown in the figures, or non-openwork pales, which are involved in mixing the components 101 and 102. These blades can be made of a single piece of material with the rod 5, or in the form of one or a plurality of parts arranged and secured so as to be rigidly connected to the end 5b of the rod 5 of the mixer 7.

At the other of the ends 5a thereof, opposite the end 5b, the rod 5 is equipped with an operating handle 6 enabling the actuation of said rod by the user, from outside the main module 1 when the mixer 7 is connected to said main module. In the example represented in the figures, the handle 6 is connected by an internal screw thread to the rod 5 at its end 5a which comprises a complementary external screw thread. The handle 6 enables, during the mixing phase, gripping and operation of the mixing unit by the user in order to provide translational and rotational movements about the longitudinal axis of the rod 5 thereto. These movements are repeated in order to mix the powder 101 and the liquid 102, for the required time and with the dynamics required to obtain a homogeneous and ready-to-use cement 100 (FIG. 5). As the distal end 1b has an opening of a diameter equal to the diameter to the cylinder formed by the internal wall of the main module, complete mixing of the powder 101 and the liquid 102 and obtaining a homogeneous cement 100 are facilitated.

The cap 4 of the mixer 7 is similar to the closing cap 2 described above, except that it comprises, for example at the center thereof, a hole 4a through which the rod 5 can slide and rotate. The hole 4a can be associated, for example, with sealing strips 4b. In one example, two of such strips enable contact water tightness with the rod 5 during its movements in the mixing body 1, therefore with respect to the cap 4 which is connected to said mixing body. In this way, the rod 5 can be actuated in water tight rotation about a longitudinal axis of said rod and in water tight translation along said longitudinal axis, in response to the actuation by the user via the handle 6. It should be noted that, when the mixing unit 7 is connected to the main module 1, the longitudinal axis of the rod 5 also corresponds to the longitudinal axis of the cylindrical body of said main module.

With reference to FIGS. 6, 7, 8, 9 and 10, a further functional module is a transfer unit, or piston 9. The function of the piston 9 is to enable the user to transfer cement 100 from the body of the main module 1 to an injection unit, or syringe, which is another accessory which will be described hereinafter. To this end, the transfer unit 12 is adapted to be connected, in a transfer phase following the mixing phase, to the proximal end 1a of the main module, instead of the mixing unit 7. This connection is made, first, while the distal end 1b of the mixing module 1 is still closed by the closing cap 2.

In the proposed kit, the transfer unit 12 is completely distinct from the mixing unit 7, in that it has no element in common therewith. In other words, the function of mixing the components of the cement until a ready-to-use homogeneous cement is obtained, on the one hand, and the function of transferring cement from the main body in which mixing was carried out to the syringe used for injecting the cement, on the other hand, are carried out by two accessories of the kit that are distinct from and independent of one another, and also distinct from the syringe per se. They are performed successively in operating phases that are also separate from and independent of one another. Nevertheless, the body of the main module 1 is associated successively with the mixing unit and then with the transfer unit. In addition, during the injection phase, it is involved in the ergonomics of the device since it can be used by the user as means for gripping the syringe.

The piston 7 comprises a cap 8, and an actuation rod 9 passing through said cap.

Like the cap 4, the cap 8 is adapted to close the proximal end 1*a* of the body of the main module when the transfer unit 12 is connected to said main module. In order to make this connection, the cap 8 can comprise a internal screw thread complementary with the external screw thread of the proximal end 1*a* of the body of the main module 1.

The actuation rod 9 is in the form of an elongated body, for example made of solid material, of cylindrical shape, with a diameter substantially less than the internal diameter of the body of the main module 1, and a length approximately equal to or greater than the length of said body along its longitudinal axis. Unlike the rod 5 of the mixer 7 which is outwardly smooth, the rod 9 of the piston 12 is threaded over a substantial part of the length thereof. Indeed, it comprises a screw thread 9*c*.

At one of its ends 9*b* intended to plunge into the body of the main module 1 when the piston 12 is connected to said main module, the actuation rod 9 comprises a piston head of cylindrical shape, having an external diameter equal to the internal diameter of the cylindrical body of the main module 1. More generally, the piston head has a cross-section with a shape complementary with that of the internal cross-section of the body of the main module 1. As the distal end 1*b* has an opening with a diameter equal to the diameter of the cylinder formed by the internal wall of the main module 1, the shape of the piston head is advantageously simple, that is to say flat. This simple shape is economical to produce and enables the user to readily transfer all the cement from the body of the main module 1 to the injection unit. In the illustrated example, this piston head is made of a single piece of material with the rod 9, and is thus also referred to hereinafter by reference sign 9*b*. However, it can also be made in the form of one or a plurality of parts arranged and secured so as to be rigidly connected to the end 9*b* of the rod 9 of the piston 12. If the cylindrical body of the main module 1 exhibits some elasticity, the external diameter of the head 9*b* of the piston can even be slightly greater than the internal diameter of said body. The piston head 9*b* comprises an annular groove where an O-ring 10 is housed, which is adapted to ensure the water tightness between the piston head and the internal wall of the cylindrical body of the main module 1.

The cap 8 of the piston 12 is similar to the cap 4 of the mixer 7 described above, except that it comprises, for example at the center thereof, a threaded hole 8*a*, complementary with the screw thread 9*c* of the body of the rod 9. The engagement of these two screw threads enables the rod 9 and therefore the piston head 9*a*, to move forwards or backwards in the cylindrical body of the module 1 according to the direction, i.e. screwing or unscrewing, wherein the rod 9 is actuated, for example operated by the user. In other words, the rotation of the rod 9 of the piston about the longitudinal axis thereof is converted into translational movement along said axis, by the effect of the abovementioned screw threads. It should be noted that, when the piston 12 is connected to the main module 1, the longitudinal axis of its rod 9 also corresponds to the longitudinal axis of the cylindrical body of said main module.

At the other of its ends 9*a*, opposite the end 9*b*, the rod 9 is equipped with an operating handle 11 enabling the actuation of said rod by the user, from outside the main module 1 when the piston 9 is connected to said main module. In the example depicted in the figures, the handle 11 is connected by an internal screw thread to the rod 9 at its end 9*a* which comprises a complementary external screw thread, which is preferably separate from the screw thread 9*c* of the body of the rod 9. Further means within the grasp of those skilled in the art, such as snap-fitting, bonding, a nut, or one or a plurality of keys can be provided in order to ensure the proper connection of the handle 11 with the rod 9, even when a rotational movement of the rod 9 is communicated by the user via the handle 11 in order to advance the piston 12.

The handle 11 enables, during the transfer phase, gripping and operation of the transfer unit by the user in order to apply a translational movement thereto along the longitudinal axis of the body of the main module 1, in order to push the cement into this body, as will now be explained.

Figure 8:
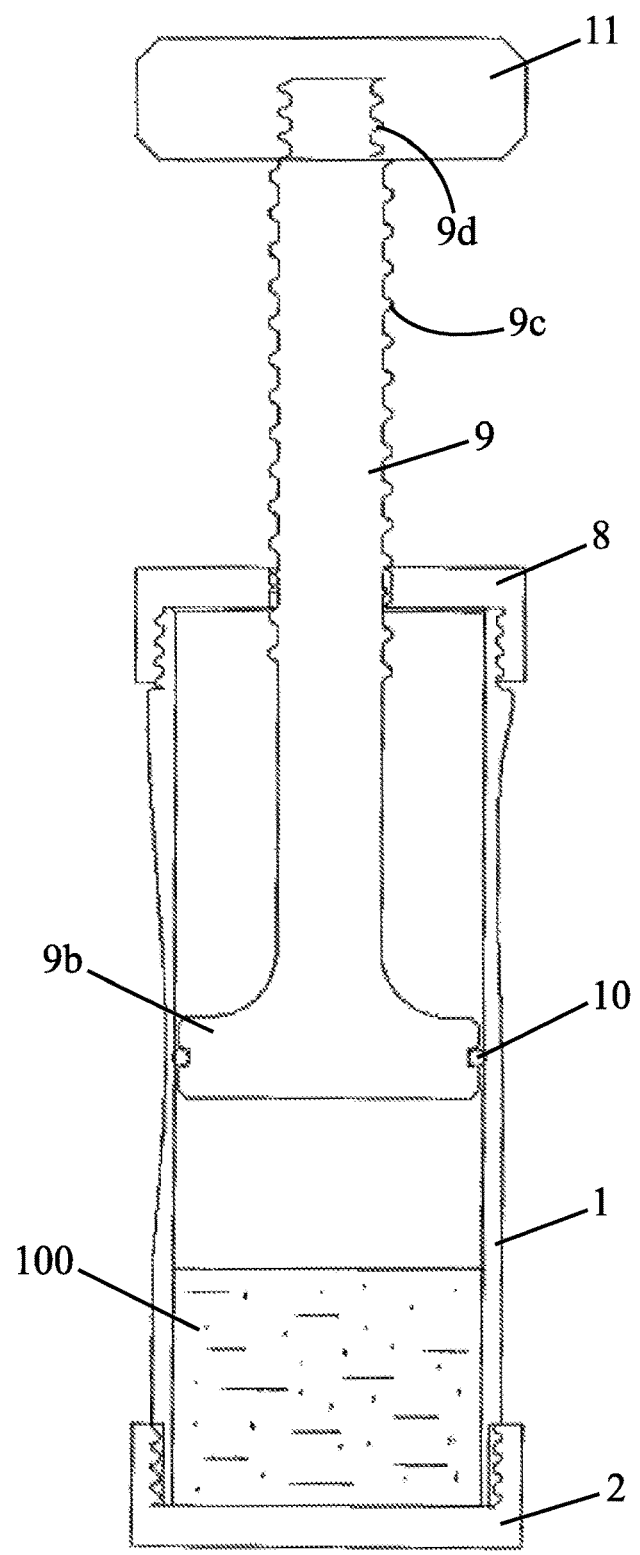
FIG. 8 is a sectional view of the transfer unit of FIG. 7 connected to the main module of FIG. 1.
Figure 9:
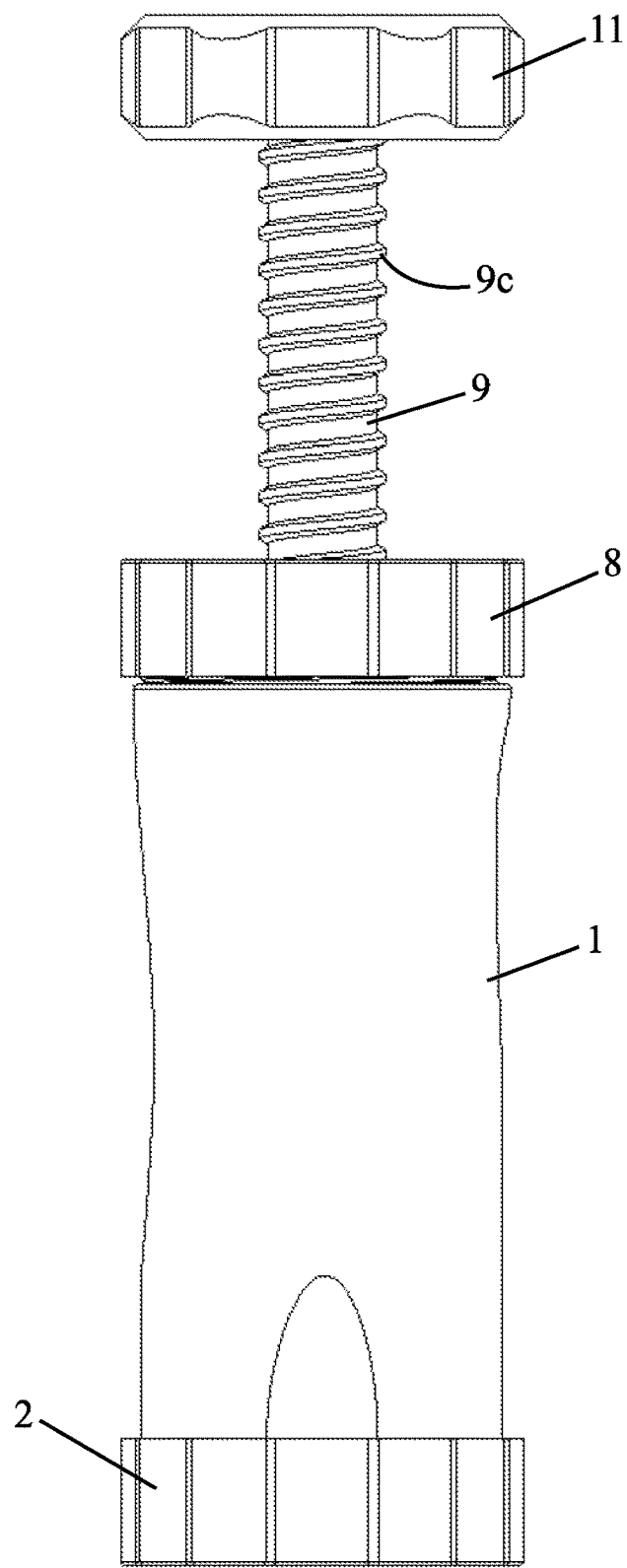
FIG. 9 is a side view of the transfer unit of FIG. 7 connected to the main module of FIG. 1.

Once the transfer unit 12 has been fastened onto the body of the main module 1 as shown in FIGS. 8 and 9, the device thus assembled can be inverted by 180° about an imaginary horizontal axis, that is to say bottom-up, or vice versa.

Figure 10:
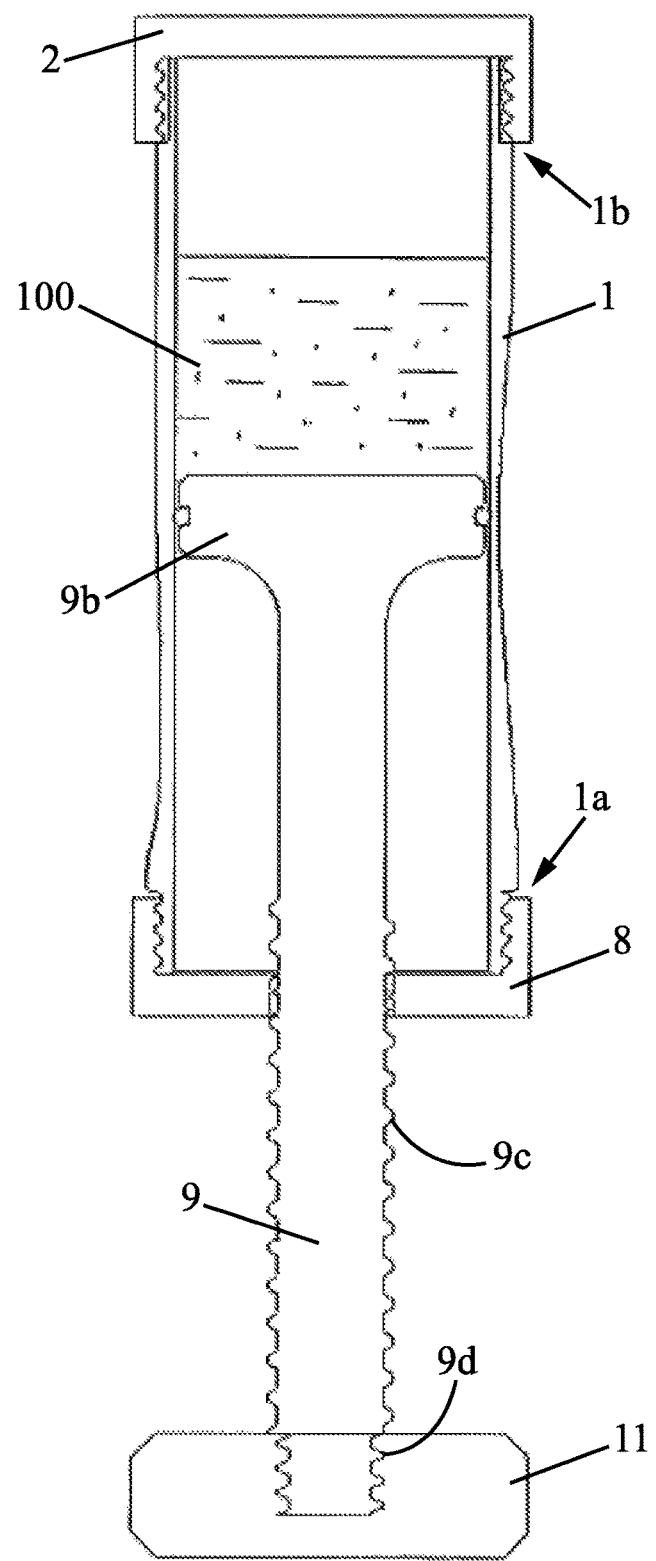
FIG. 10 is a sectional view of the transfer unit of FIG. 7 connected to the main module of FIG. 1, after top/bottom inversion.
Figure 11:
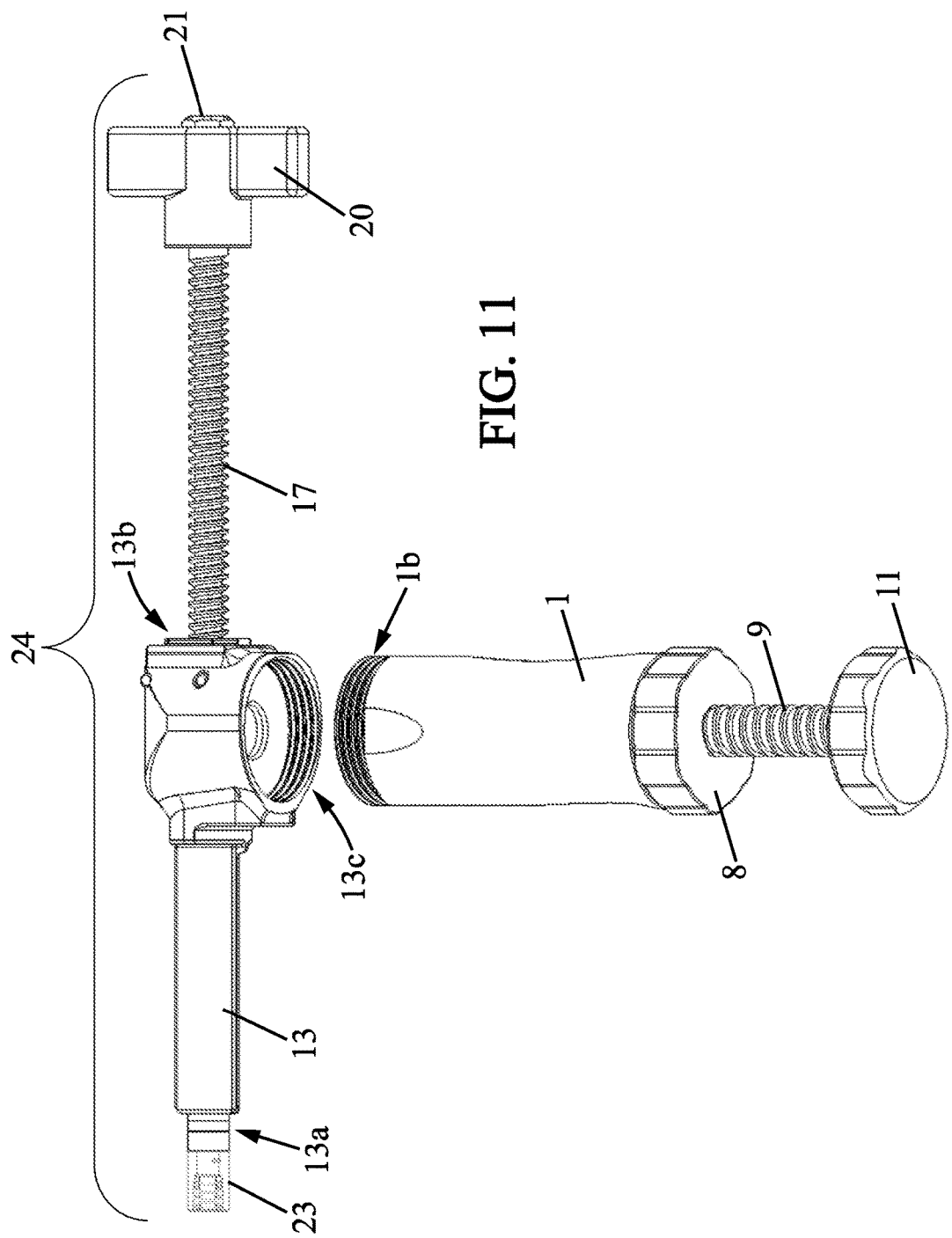
FIG. 11 is a three-dimensional view of the transfer unit of FIG. 7 connected to the main module of FIG. 1, and of an embodiment of the injection unit.
Figure 12:
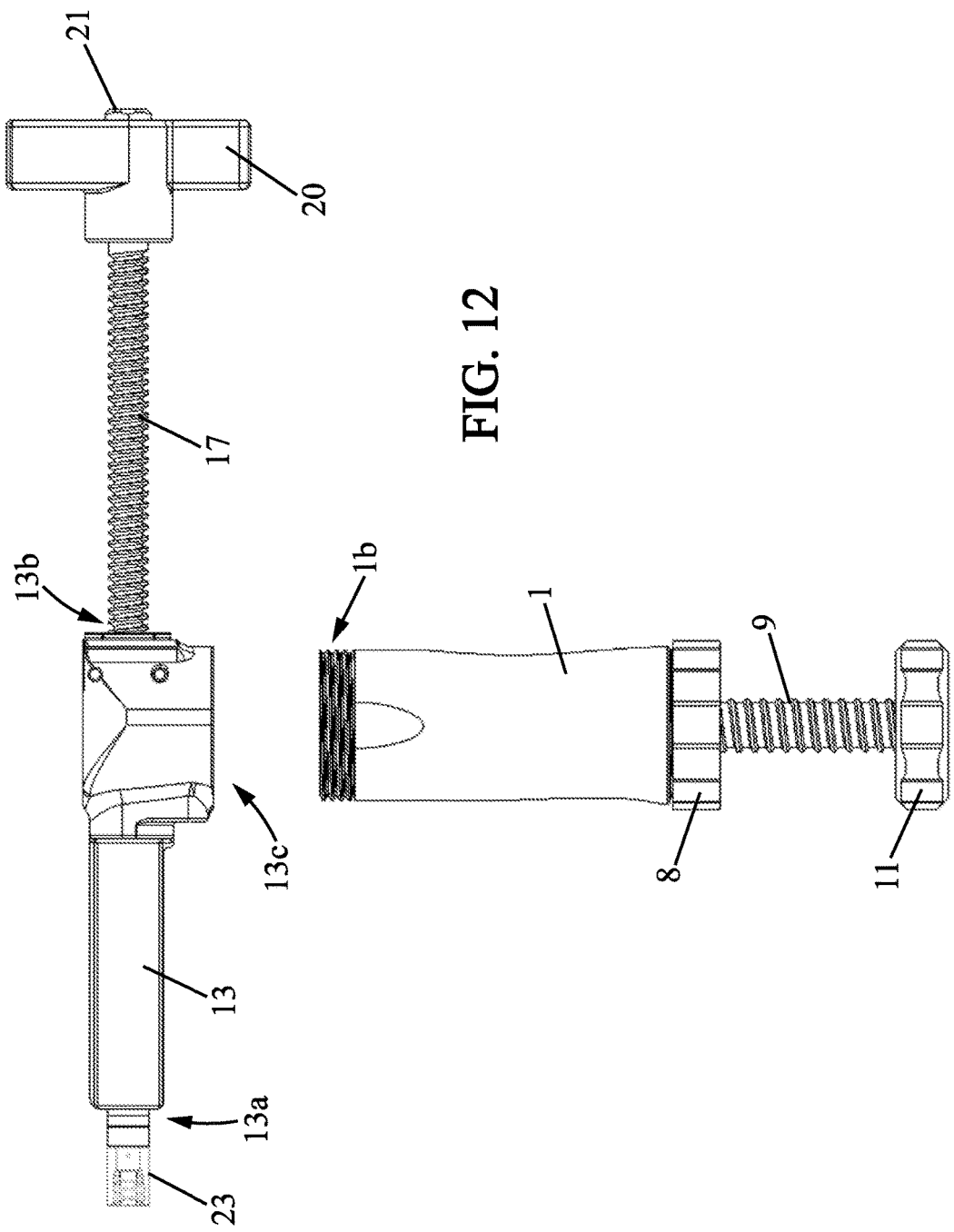
FIG. 12 is a side view of the same elements as of FIG. 11.
Figure 13:
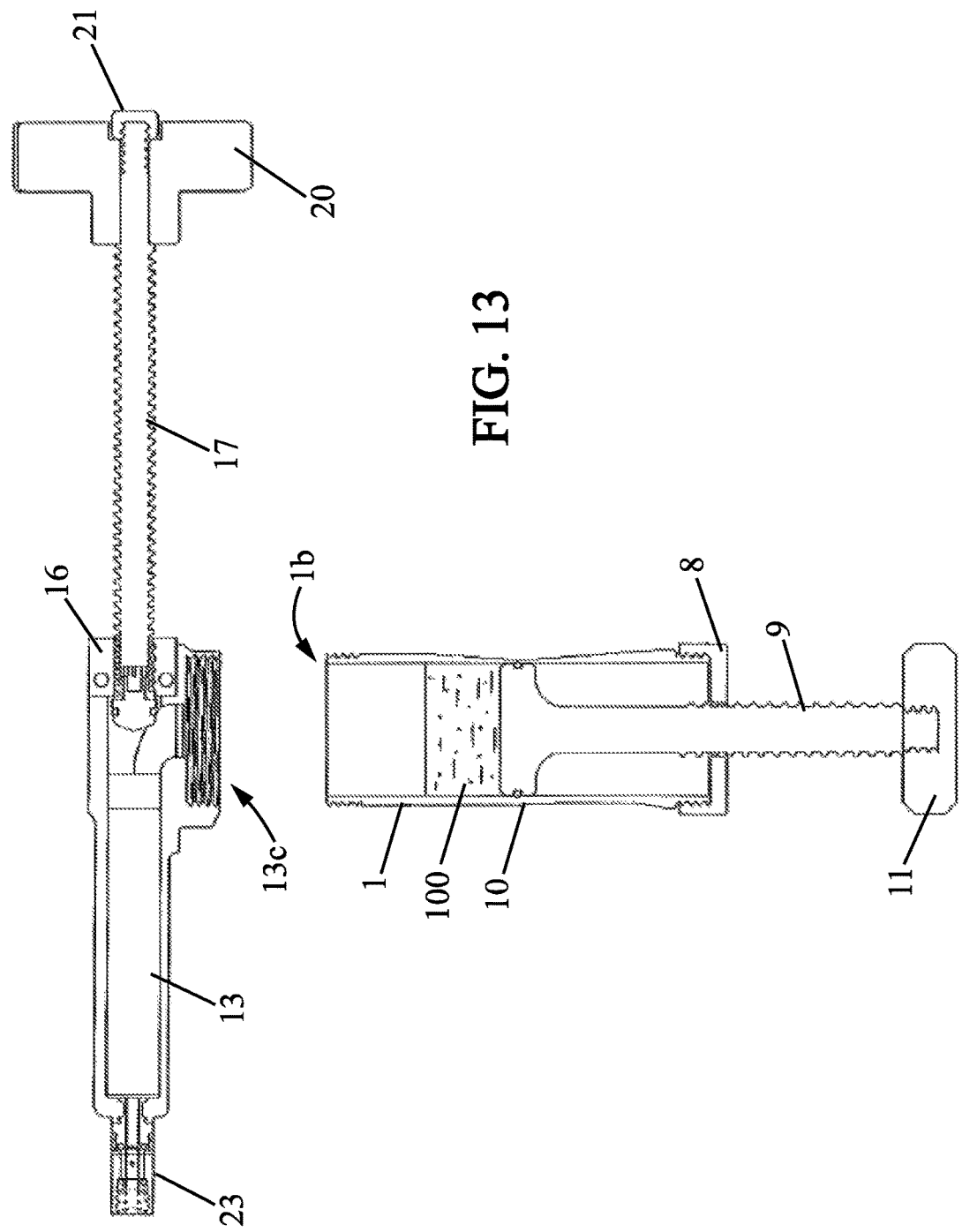
FIG. 13 is a sectional view of the elements of FIG. 12.

The device inverted in this way as shown in FIG. 10, the cement 100 falls gravitationally against the piston head 9*a*. The closing cap 2 can then be removed from the distal end 1*b* of the mixing body 1, to continue the operations using the last accessory of the kit.

Indeed, the kit further comprises a further functional module, as an accessory of the main module, that is to say an injection unit or syringe, which will now be described with reference to FIGS. 11, 12, 13, 14 and 15.

This injection unit 24 is suitable for being connected, in the transfer phase as well as in an injection phase following the transfer phase, to the distal end 1*b* of the main module instead of the closing cap 2. Connected in this way, it can receive the cement transferred from the main module, during the transfer phase. Subsequently, during the injection phase, it enables the user to inject the bone cement to the target site, for example the vertebra to be treated.

In the embodiment as depicted, the injection unit 24 comprises a main body 13 of elongated shape, with an internal chamber adapted to receive bone cement ready to be injected.

Figure 20:
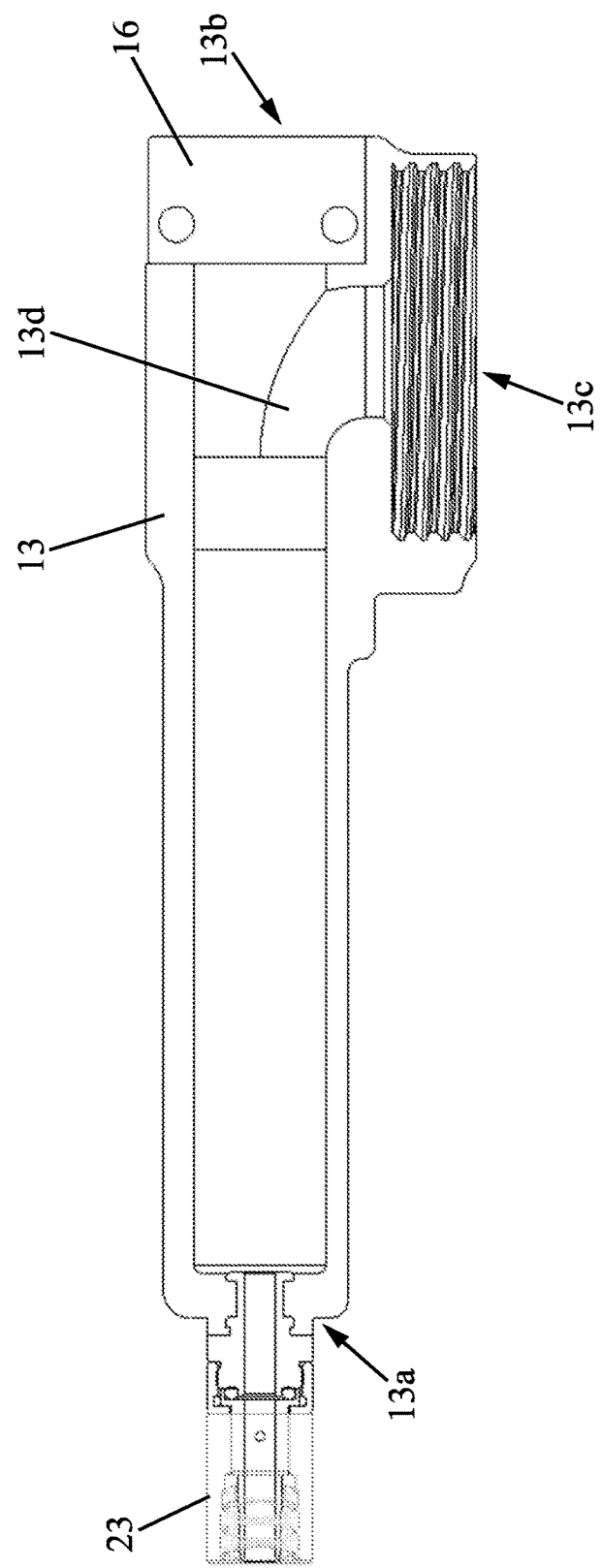
FIG. 20 is a sectional view of the elongated body of the injection unit of FIG. 11.

With reference to FIG. 20, the main body 13 of the injection unit 24 has three openings 13*a*, 13*b* and 13*c*. The two openings 13*a* and 13*c*, which are at the respective ends of the main body 13, each have a passage axis arranged along the longitudinal axis of said body 13, respectively for the cement coming out from said body to the outside of the syringe, and for the threaded rod of the piston 22.

The third opening 13*c* has a passage for the bone cement wherein the axis is secant, for example perpendicularly, with the longitudinal axis of the body 13. The opening 13*c* is a bone cement inlet adapted to admit the cement into the internal chamber of said main body 13 from the mixing body of the main module 1. To this end, the opening 13*c* of the main body 13 is threaded so as to be connected by screwing at the distal end 1*b* to the mixing body 1, as shown in FIGS. 11, 12, 13, 14 and 15. The intake of bone cement is carried out when the transfer unit 12 is connected to the proximal end 1*a* of the main module 1, and is actuated by the user in order to push the cement 100 in the mixing body towards the distal end 1*b* of said main module, whereas said distal end is connected to the inlet 13*c* of the syringe as described above.

As the distal end 1*b* has an opening with a diameter equal to the diameter of the cylinder formed by the internal wall of the main module 1, the connection between said main module and the injection unit 24 is mechanically reinforced. Consequently, during the transfer and injection phases, the user can advantageously grip the main body 1 as a handle, in the manner of a gun, without being concerned that the device according to the present invention could break.

The opening 13*a* is a bone cement outlet adapted to, in the bone cement injection phase, dispense the bone cement 100 outside the injection unit 24, in response to an action of the user. To this end, the opening 13a of the main body 13 is molded with a "luer-lock" type connection 23, this connection enabling the connection of the syringe to further medical devices which can be used during the surgical procedure, particularly injection nozzles of varied shapes and cross-sections.

Finally, the opening 13b is adapted to let a piston rod to extend therethrough. Indeed, the syringe 24 also comprises a piston 22 shown in FIG. 18. The piston 22 includes a piston head 18, as well as a rod 17 for actuating said piston head, for example a threaded rod. The piston head 13 is adapted to push towards the outlet 13a the bone cement which is situated in the internal chamber of the main body 13 of the syringe. To this aim, the piston head 18 is moved in the main body 13, from the opening 13b to the outlet 13a, via the actuation rod 17 which can be actuated by the user from outside the injection unit 24. This operation triggers the movement of the piston head 18 in the internal chamber of the main body 13 with the effect of pushing the bone cement towards the outlet 13a.

Figure 18:
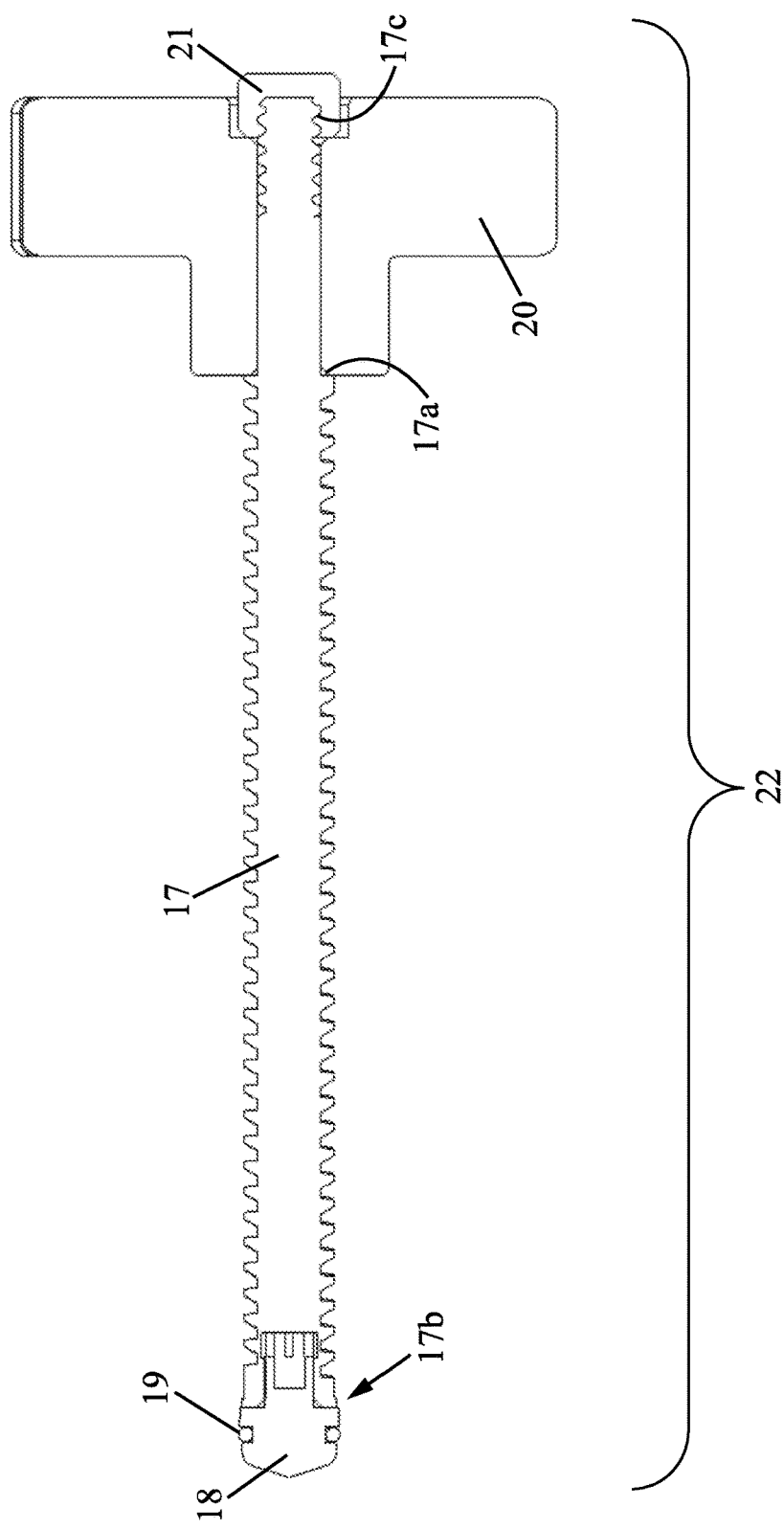
FIG. 18 is a sectional view of the piston of the injection unit of FIG. 11.

With reference in particular to FIG. 18, the threaded rod 17 has at the end 17a of the screw thread which is opposite the piston head 18, a shoulder enabling the positioning of a gripping and operating handle 20. The handle 20 can be held in position by means of a nut 21 screwed onto a further screw thread 17c at the terminal end of the rod 17. The rod 17 has a further shoulder at the end 17b thereof on the piston head 18 side, this shoulder receiving an end piece 18 which is locked into the rod 17 against this shoulder. This end piece 18 has an annular groove where an O-ring 19 is fitted, ensuring the water tightness of the piston head 18 in the main body 13 of the syringe 24.

Figure 19:
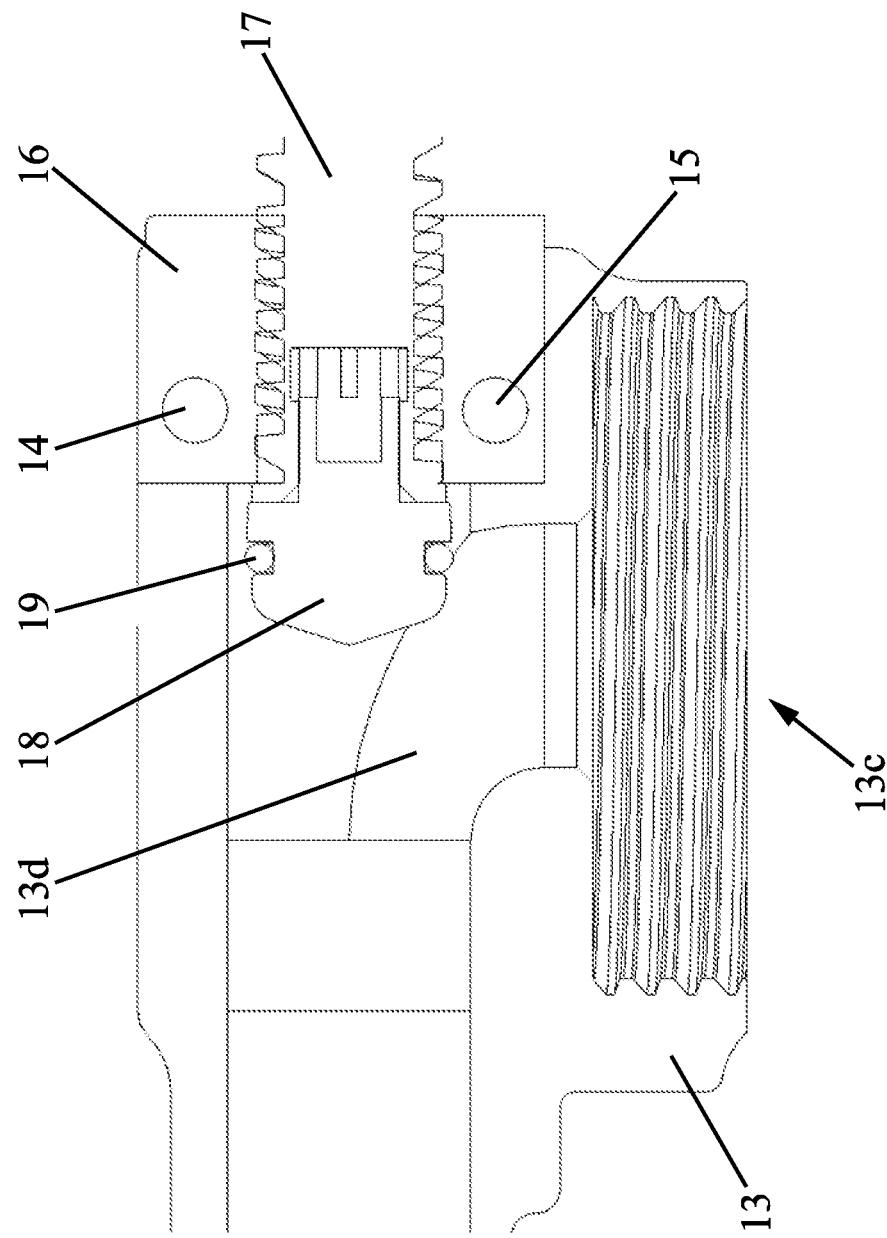
FIG. 19 is a sectional view of a detail of the piston head of the piston of the injection unit of FIG. 11.

With reference to FIG. 19, the opening 13b opposite the outlet 13a along the longitudinal axis of the main body 13 of the syringe 24 receives an intermediate part 16 by means of which the threaded rod 17 of the piston 22 is connected to said main body of the syringe.

In the depicted example, the intermediate part 16 includes a threaded central hole, this internal screw thread being complementary with the screw thread of the rod 17. Furthermore, the intermediate part 16 is connected to the main body 13 of the syringe 24 by two cylindrical rods, for example made of steel, 14 and 15 respectively. Further embodiments of this connection are nonetheless possible, such as bonding, welding, snap-fitting or force-fitting, depending on the materials of which the various elements of the kit are made.

The use of the syringe 24 of the device is as follows.

Figure 14:
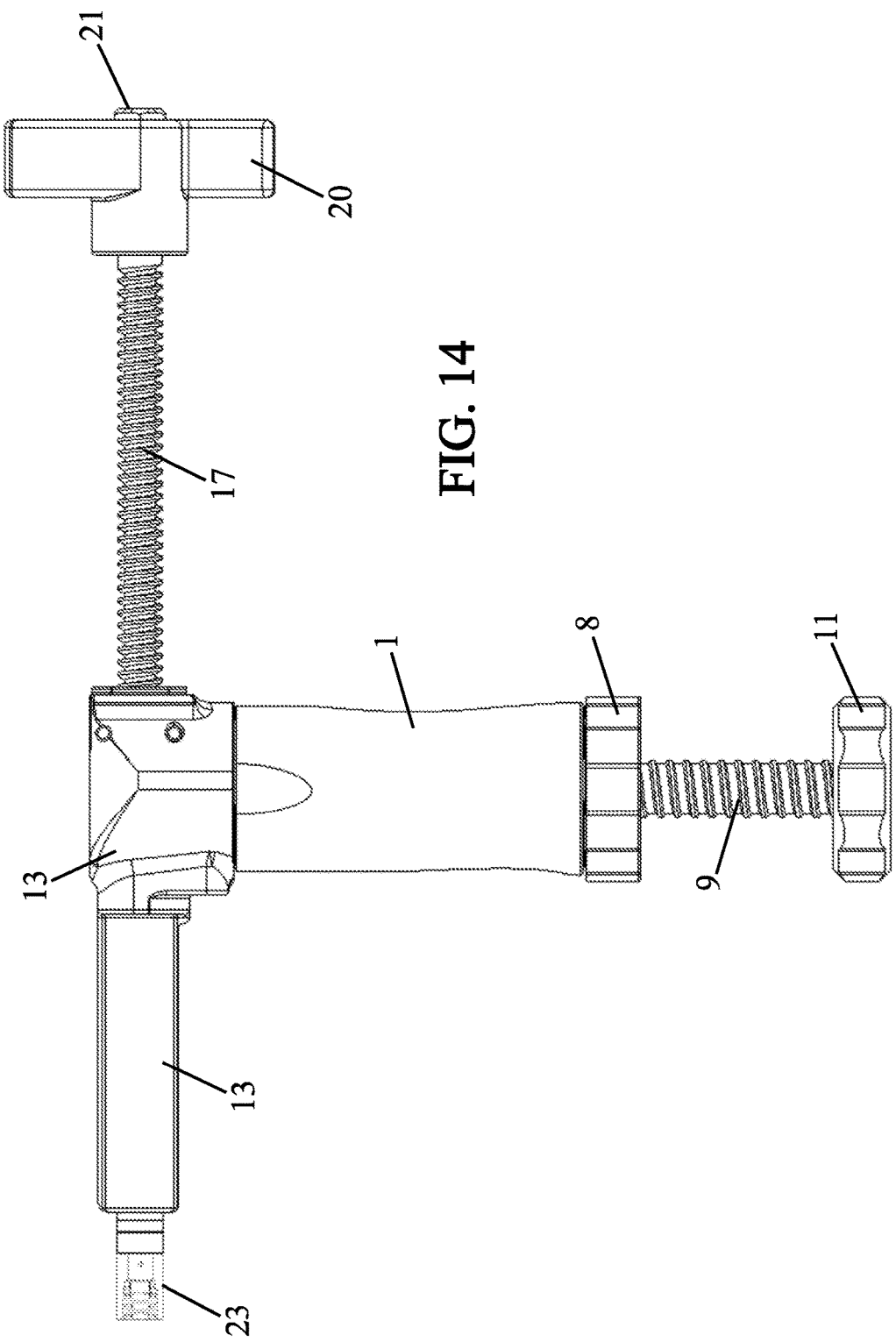
FIG. 14 is a side view of the transfer unit of FIG. 7 connected to the main module of FIG. 1, and of the injection unit of FIG. 11 also connected to said main module.
Figure 15:
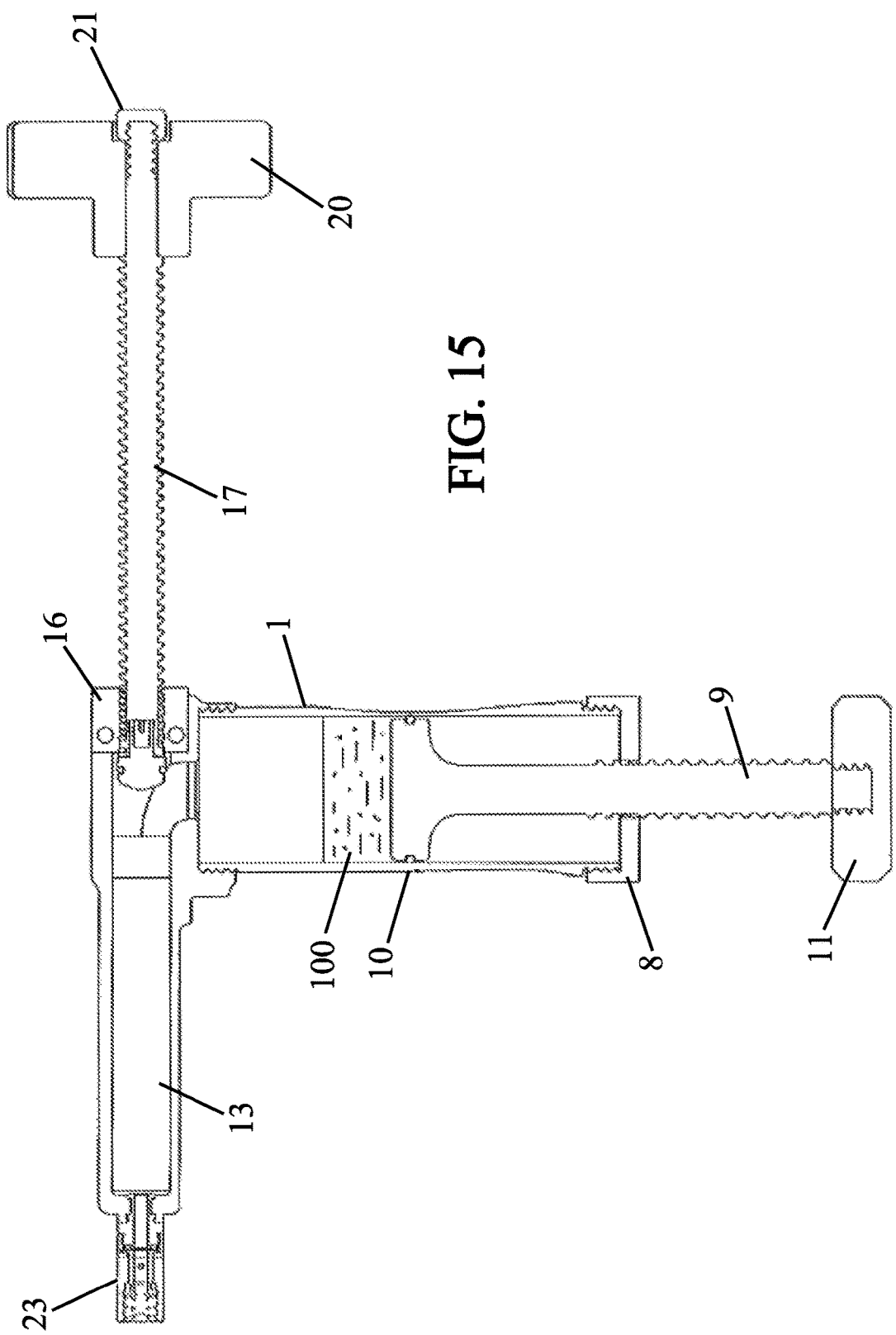
FIG. 15 is a sectional view corresponding to the view in FIG. 14, before the start of the transfer phase.
Figure 16:
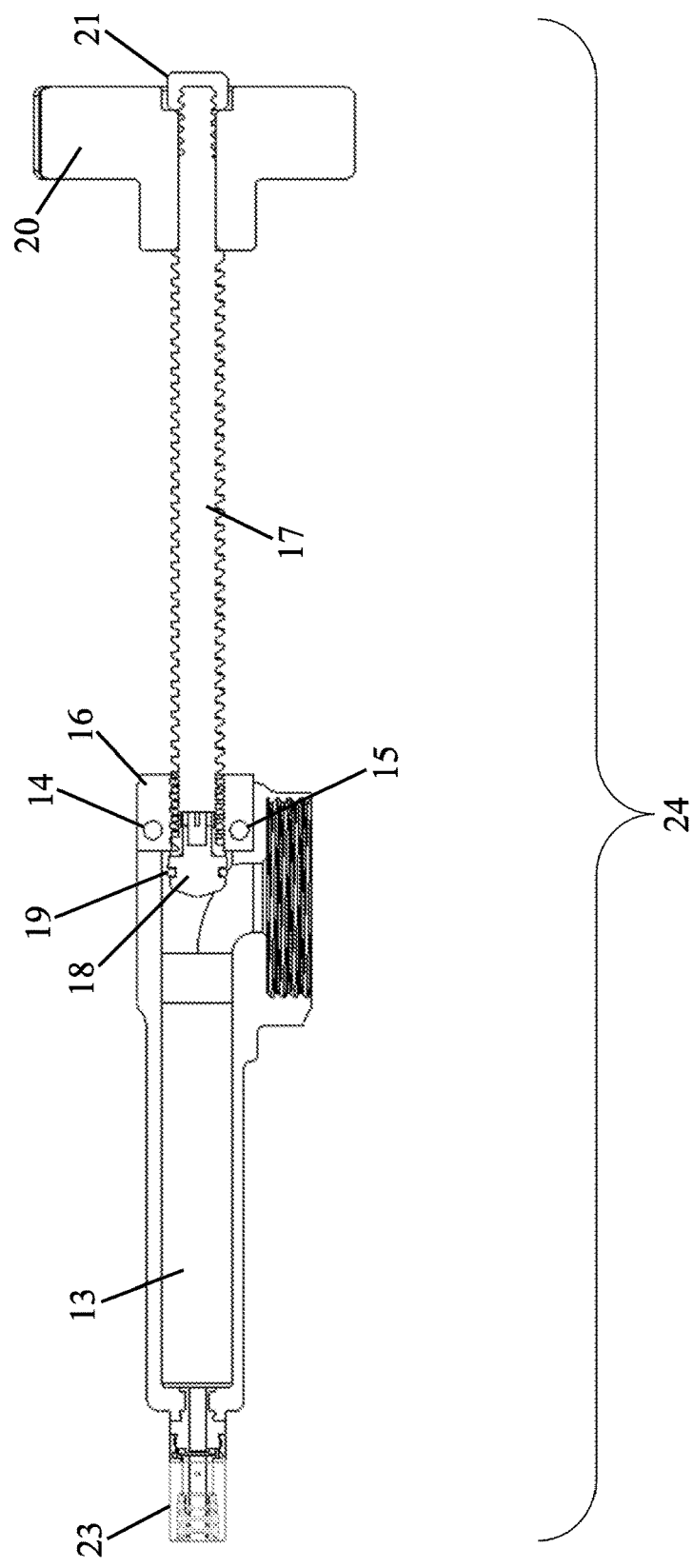
FIG. 16 is a sectional view of the injection unit of FIG. 11.
Figure 17:
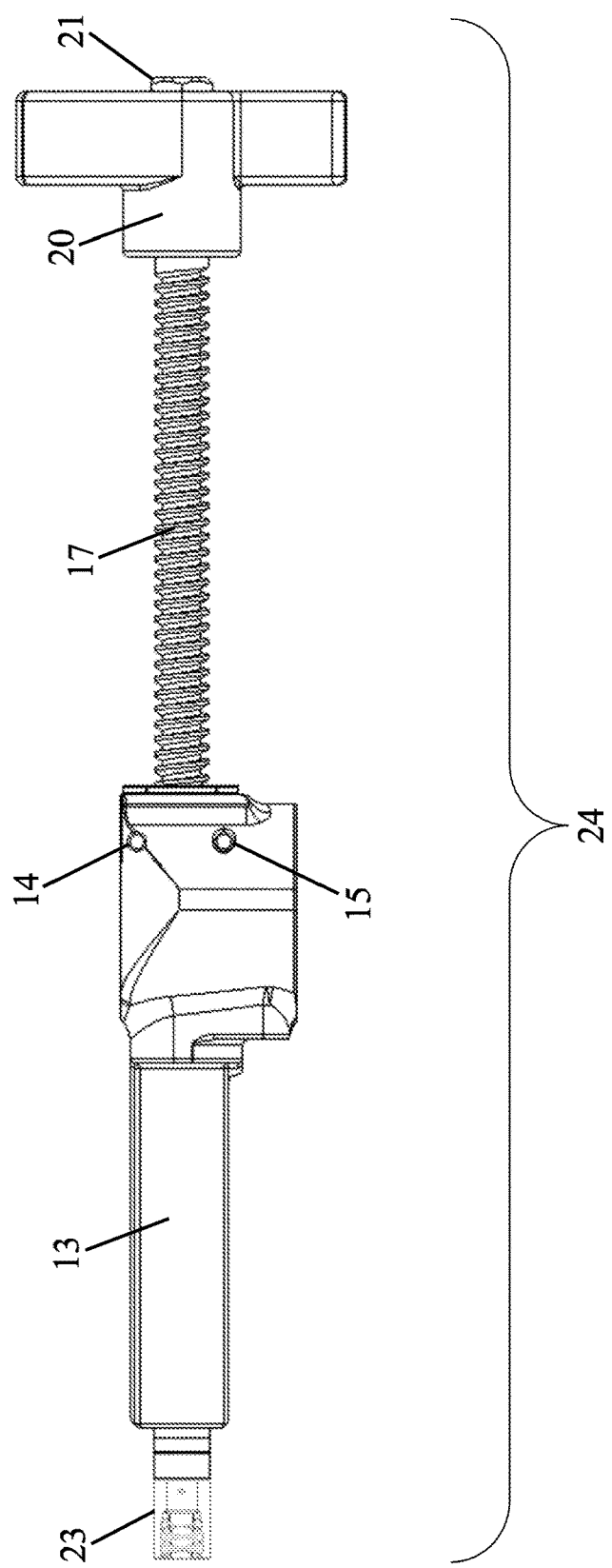
FIG. 17 is a side view of the injection unit of FIG. 11.

Once the syringe 24 and the mixing body 1 have been connected together, as shown in FIGS. 14 and 15, the bone cement can be transferred from the mixing body 1 into the main body 13 of the syringe, during the transfer phase. This transfer is obtained by screwing the piston 9 via the handle 11 of the transfer unit 12, which induces the movement of the piston 9 in the mixing body 1 along the longitudinal axis thereof.

Figure 21:
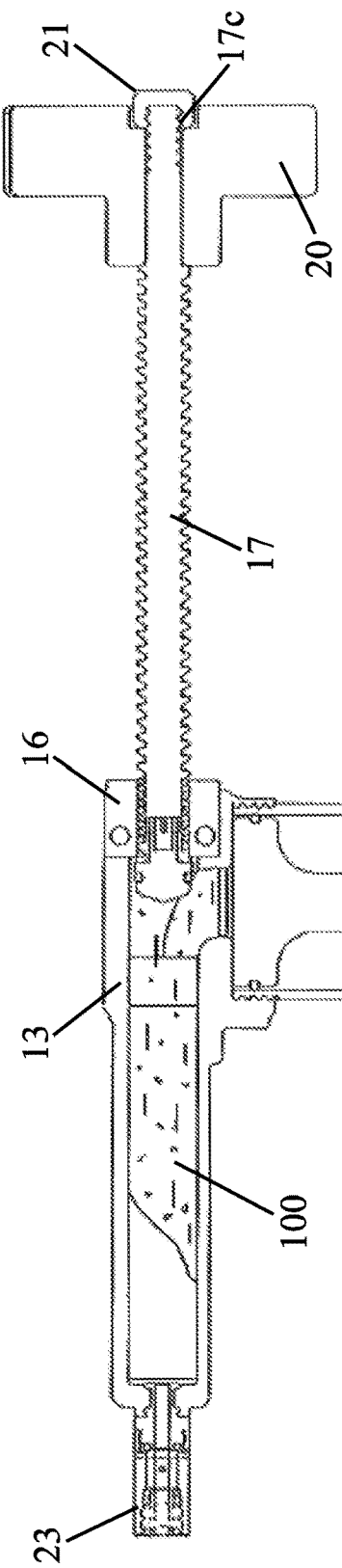
FIG. 21 is a sectional view showing the same elements as of FIG. 15, after the transfer phase but before the injection phase; and, FIG. 22 is a sectional view showing the same elements as FIG. 15, in a configuration of the kit when it is ready for injection.

Once the bone cement has been entirely transferred into the volume of the main body 13 of the syringe 24, as shown in FIG. 21, the device is ready for the injection of the bone cement into the vertebral body of the vertebra to be treated.

Figure 22:
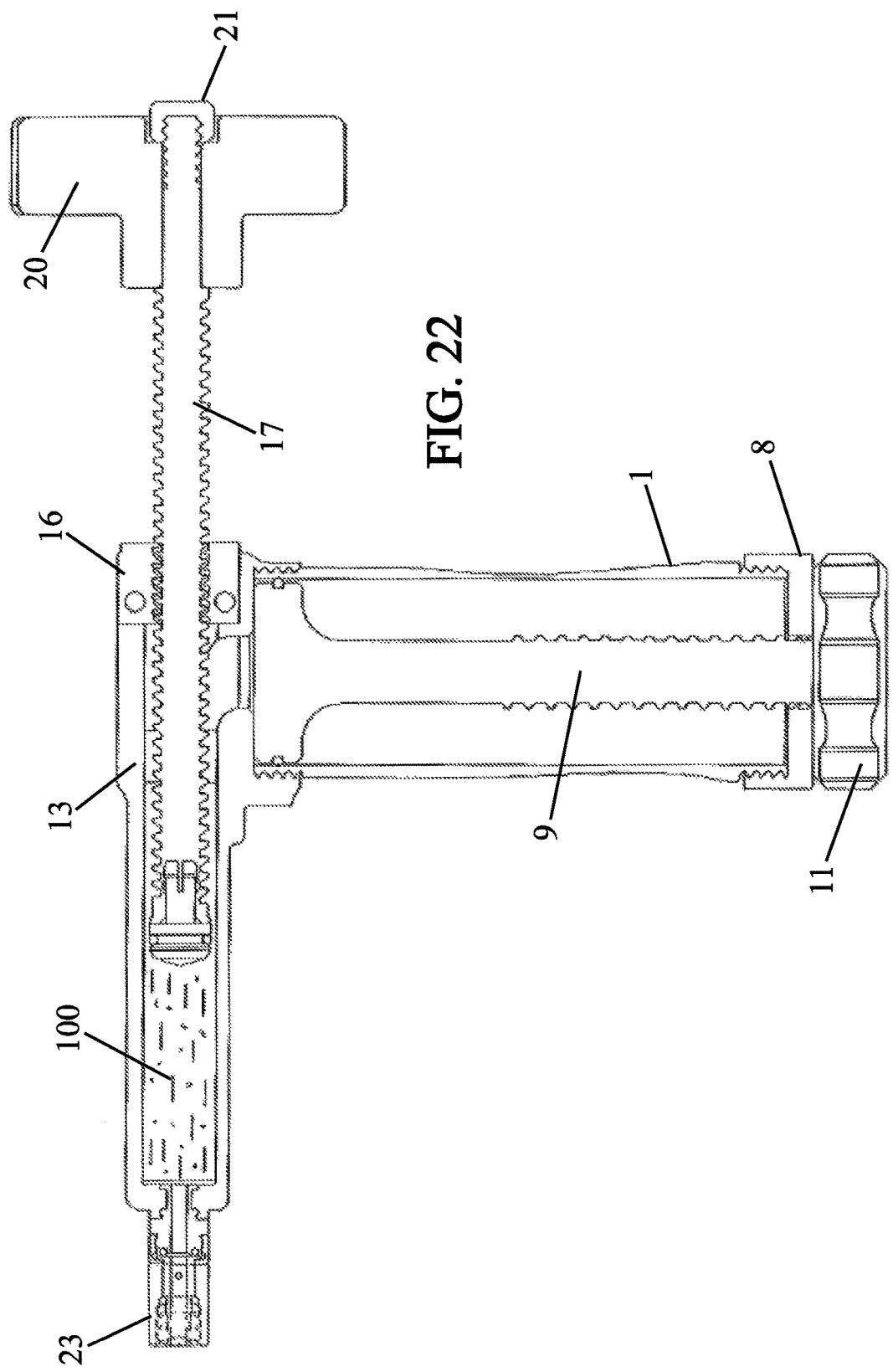

The injection is then performed, during the injection phase, by applying a rotation movement on the handle 20, said movement causing the translation of the piston 22 of the syringe. This has the effect of pushing the bone cement 100 into the main body 13 of the syringe 24, along the longitudinal axis thereof, up to the outlet 13a as shown in FIG. 22.

In one embodiment, illustrated in particular by FIGS. 19, 20 and 21, the injection unit comprises an angled channel 13d, having an inlet coupled with the bone cement inlet 13c and an outlet leading to the internal chamber of the main body 13 oriented towards the bone cement outlet 13a. This channel 13d has an opening at the angle, said opening being adapted so that the piston head 18 goes therethrough to enable the bone cement 100 to be pushed towards the bone cement outlet 13a.

In some embodiments, the mixing body of the main module 1 and/or the main body 13 of the injection unit 24 can be made of transparent material, such as polycarbonate, in order to enable the user to observe the cement. In particular, the user can thereby make sure, by a mere visual check, of the homogeneity and viscosity of the cement, particularly during the mixing phase, and the progression thereof during the transfer phase and during the injection phase, respectively.

The present invention has been described and illustrated in the detailed description and in the Figures. The present invention is not limited to the embodiments presented herein. Further variants and embodiments can be inferred and implemented by those skilled in the art on reading the present description and the appended Figures.

In the claims, the term "comprise" does not exclude further elements or further steps. The various features presented and/or claimed can be advantageously combined. The presence thereof in the description or in different dependent claims, does not exclude this possibility. The reference signs should not be understood as limiting the scope of the invention.

The invention claimed is:

1. A kit-type device for mixing and injecting a bone cement, comprising a main module, on the one hand, and accessories comprising a removable closing cap and a plurality of functional modules, on the other hand, said accessories being adapted to be each connected or not to the main module of respective phases of use of the device, wherein:
   the main module is a hollow cylindrical body having an internal wall, an open proximal end and an open distal end, adapted to be each connected to one or a plurality of the accessories of the device, of the phases of use, the distal end (1b) comprising an opening with a diameter equal to the diameter of the cylinder formed by the internal wall of the hollow cylindrical body;
   one of the functional modules is a mixer, adapted to be connected, in a mixing phase, to the proximal end of the main module while the distal end of said main module is closed by the closing cap, and to enable a user to mix at least two compounds of the bone cement in the body of the main module;
   a further functional module is an injector, adapted to be connected, in a transfer phase following the mixing phase as well as in an injection phase following said transfer phase, to the distal end of the main module instead of the closing cap, and to enable the user to inject the bone cement;
   a further still functional module, distinct from the mixer and with no common element with the mixer, is a transferor, adapted to be connected, in the transfer phase, to the proximal end of the main module instead of the mixer and to enable the user to transfer bone cement from the body of the main module to the injector.

2. The kit-type device of claim 1, wherein the accessories further comprise a funnel, adapted to enable, before the mixing phase, pouring via the proximal end of the main module of the compounds of the bone cement to be mixed in the body of said main module, while the distal end of the main module is closed by the closing cap.

3. The kit-type device of claim 1, wherein the mixer and the transferor each comprise a cap and an actuation rod passing through said cap, the cap of each of mixer, injector and transferor being adapted to close the proximal end of the body of the main module when the corresponding one of mixer, injector or transferor is connected to said main module.

4. The kit-type device of claim 3, wherein:
the actuation rod of the mixer comprises mixing blades at a first end of said rod intended to plunge into the body of the main module, as well as a gripping handle at a second end of said rod enabling actuation by the user from outside the main module; and,
the cap of the mixer comprises a hole associated with sealing strips, through which the rod of the mixer can be actuated in water tight rotation about a longitudinal axis of said rod and in water tight translation along a longitudinal axis of the cylindrical body of the main module, in response to the actuation by the user via the handle of said rod.

5. The kit-type device of claim 3, wherein:
the actuation rod of the transferor is threaded on at least a part of the length thereof and comprises a piston head at a first end of said rod intended to plunge into the body of the main module, as well as a gripping handle at a second end of said rod enabling actuation by the user from outside the main module;
the piston head has a cross-section with a shape complementary with the shape of the internal cross-section of the body of the main module and is provided with a peripheral groove receiving a seal; and
the cap of the transferor comprises a threaded hole to connect the actuation rod of the transferor to the cap of said transferor, when engaging with the screw thread of said rod, and whereby said rod can be actuated by screwing/unscrewing to operate the piston in response to the actuation by the user via the handle of said rod.

6. The kit-type device of claim 3, wherein the main module comprises, at the proximal end thereof, a screw thread adapted to engage with a complementary screw thread of the respective caps of the mixer and the transferor.

7. The kit-type device of claim 1, wherein the injector comprises:
an elongated body with an internal chamber adapted to receive bone cement ready for injection;
a bone cement inlet, adapted to admit bone cement into the internal chamber from the body of the main module, when the transferor is connected to the distal end of said main module and is actuated by the user;
a piston head as well as an actuation rod of said piston head which can be actuated by the user from outside the transferor to operate said piston head in the internal chamber of the elongated body in order to push the bone cement; and,
a bone cement outlet, adapted to dispense the bone cement outside the transferor in response to an action by the user via the actuation rod of the piston head.

8. The kit-type device of claim 7, wherein the injector comprises an angled channel, having an inlet coupled with the bone cement inlet and an outlet leading to the internal chamber of the elongated body oriented towards the bone cement outlet, as well as an opening at the angle of the channel, said opening being adapted so that the piston head passed therethrough to enable the bone cement to be pushed towards said bone cement outlet.

9. The kit-type device of claim 7, wherein the main module comprises, at the distal end thereof, a screw thread adapted to engage with a complementary screw thread of the injector at the inlet of said injector, to ensure the connection of the injector to the main module.

10. The kit-type device of claim 1, wherein the distal end has an opening having a diameter equal to the diameter of a cylinder formed by an internal wall of the main module.

11. Method for mixing and injecting a bone cement using a kit-type device comprising a main module with the shape of a hollow cylindrical body having an internal wall, an open proximal end and an open distal end with a diameter equal to the diameter of the cylinder formed by the internal wall of the hollow cylindrical body (1), on the one hand, and accessories comprising a removable closing cap and a plurality of functional modules, on the other hand, the method comprising:
a) in a mixing phase, connecting one of the functional modules or mixer to the proximal end of the main module while the distal end of said main module is closed by the closing cap, and mixing at least two compounds of the bone cement in the body of the main module;
b) in a transfer phase following the mixing phase:
b1) connecting a further functional module or transferor, distinct from the mixer and with no common element with the mixer, to the proximal end of the main module instead of the mixer, and
b2) connecting a further functional module or injector to the distal end of the main module instead of the closing cap,
b3) transferring bone cement from the body of the main module to the injector; and,
c) in an injection phase following the transfer phase, injecting the bone cement.

* * * * *